United States Patent
Walter et al.

(10) Patent No.: US 7,384,941 B2
(45) Date of Patent: Jun. 10, 2008

(54) 2-(PHENOXYMETHYL)-AND 2-(PHENYLTHIOMETHYL)-MORPHOLINE DERIVATIVES FOR USE AS SELECTIVE NOREPINEPHRINE REUPTAKE INHIBITORS

(75) Inventors: Magnus Wilhelm Walter, Basingstoke (GB); Barry Peter Clark, Basingstoke (GB); Peter Thaddeus Gallagher, Basingstoke (GB); Helen Louise Haughton, Basingstoke (GB); Hélène Catherine Eugénie Rudyk, Basingstoke (GB)

(73) Assignee: Eli Lilly and Company, Indianapolis, IN (US)

( * ) Notice: Subject to any disclaimer, the term of this patent is extended or adjusted under 35 U.S.C. 154(b) by 481 days.

(21) Appl. No.: 10/524,650

(22) PCT Filed: Aug. 18, 2003

(86) PCT No.: PCT/US03/23269

§ 371 (c)(1),
(2), (4) Date: Feb. 17, 2005

(87) PCT Pub. No.: WO2004/017977

PCT Pub. Date: Mar. 4, 2004

(65) Prior Publication Data
US 2006/0035894 A1    Feb. 16, 2006

(30) Foreign Application Priority Data
Aug. 23, 2002  (GB) .................. 0219690.5

(51) Int. Cl.
A61K 31/5377    (2006.01)
C07D 265/30     (2006.01)

(52) U.S. Cl. .................. 514/239.2; 544/158
(58) Field of Classification Search ........... 544/158; 514/239.2
See application file for complete search history.

(56) References Cited

U.S. PATENT DOCUMENTS 6,274,579 B1    8/2001    Morgan et al.

FOREIGN PATENT DOCUMENTS

| EP | 0 721 777 A3 | 7/1996 |
| EP | 0 756 869 A3 | 2/1997 |
| GB | 1 295 447 A | 11/1972 |
| GB | 1 412 546 A | 11/1975 |
| GB | 2 167 407 A | 5/1986 |
| WO | WO 99/15177 | 4/1999 |
| WO | WO 99/64009 | 12/1999 |
| WO | WO 00/39091 | 7/2000 |
| WO | WO 00/50380 | 8/2000 |
| WO | WO 01/01973 A3 | 1/2001 |

OTHER PUBLICATIONS

FDA mulls drug to slow late-stage Alzheimer's [online], [retrieved on Sep. 23, 2003]. Retrieved from the internet, URL<http://www.cnn.com/2003/HEALTH/conditions/09/24/alzheimers.drug.ap/index.html>.*
Cecil Textbook of Medicine, 20th edition (1996), vol. 2, pp. 1992-1996.*
Boot et al. "*Discovery and structure-activity relationships of novel selective norepinephrine and dual serotonin/norepinephrine reuptake inhibitors*", Bioorganic & Medicinal Chemistry Letters, 2005, vol. 15,, pp. 699-703.

* cited by examiner

*Primary Examiner*—Rebecca L Anderson
(74) *Attorney, Agent, or Firm*—Charles E. Cohen; Tonya L. Combs; Thomas E. Jackson

(57) ABSTRACT

Compounds of formula (I):

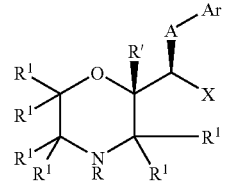

wherein A is S or O; R is H; Ar is an optionally substituted phenyl group; X is an optionally substituted phenyl group, a $C_1$-$C_4$ alkyl, a $C_3$-$C_6$ cycloalkyl group or a $CH_2(C_3$-$C_6$ cycloalkyl) group; R' is H or $C_1$-$C_4$ alkyl; and each $R^1$ is independently H or $C_1$-$C_4$ alkyl; and pharmaceutically acceptable salts thereof are selective inhibitors of norepinephrine reuptake.

8 Claims, No Drawings

2-(PHENOXYMETHYL)-AND 2-(PHENYLTHIOMETHYL)-MORPHOLINE DERIVATIVES FOR USE AS SELECTIVE NOREPINEPHRINE REUPTAKE INHIBITORS

This application is a 371 of PCT/US03/23269 filed 18 Aug. 2003.

This invention relates to novel morpholine compounds, and to their use in selectively inhibiting norepinephrine reuptake.

Selective inhibition of norepinephrine reuptake is a relatively new mode of action for the treatment of affective disorders. Norepinephrine appears to play an important role in the disturbances of vegetative function associated with affective, anxiety and cognitive disorders. Atomoxetine hydrochloride is a selective inhibitor of norepinephrine reuptake, and is marketed for the treatment of attention deficit hyperactivity disorder (ADHD). Reboxetine is also a selective norepinephrine reuptake inhibitor and is marketed for the treatment of depression. WO99/15177 discloses the use of Reboxetine to treat ADHD and WO01/01973 discloses the use of S,S-Reboxetine to treat ADHD.

According to the present invention there is provided a compound of formula (I)

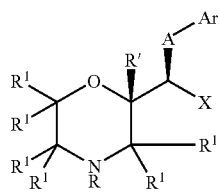

(I)

wherein:
A is S or O;
R is H;
Ar is a phenyl group optionally substituted with 1, 2, 3, 4 or 5 substituents each independently selected from $C_1$-$C_4$ alkyl, O($C_1$-$C_4$ alkyl), S($C_1$-$C_4$ alkyl), halo, hydroxy, $CO_2$($C_1$-$C_4$ alkyl), pyridyl, thiophenyl and phenyl optionally substituted with 1, 2, 3, 4 or 5 substituents each independently selected from halo, $C_1$-$C_4$ alkyl, or O($C_1$-$C_4$ alkyl);
X is a phenyl group optionally substituted with 1, 2, 3, 4 or 5 substituents each independently selected from halo, $C_1$-$C_4$ alkyl, or O($C_1$-$C_4$ alkyl); a $C_1$-$C_4$ alkyl group; a $C_3$-$C_6$ cycloalkyl group or a $CH_2$($C_3$-$C_6$ cycloalkyl) group;
R' is H or $C_1$-$C_4$ alkyl;
each $R^1$ is independently H or $C_1$-$C_4$ alkyl;
wherein each above-mentioned $C_1$-$C_4$ alkyl group is optionally substituted with one or more halo atoms;
or a pharmaceutically acceptable salt thereof;
with the proviso that, when A is O, X is a $C_1$-$C_4$ alkyl group, a $C_3$-$C_6$ cycloalkyl group or a $CH_2$($C_3$-$C_6$ cycloalkyl) group.

For the compounds of formula (I) above, it is preferred that A is S.

For the compounds of formula (I) above, it is preferred that Ar is phenyl substituted with 1, 2, 3, 4 or 5 substituents, more preferably with 1 or 2 substituents. When Ar is a substituted phenyl, it is preferred that not more than one of those substituents is a pyridyl, thiophenyl or optionally substituted phenyl group.

Preferred compounds of formula (I) above are those wherein Ar is ortho-substituted.

In a further preferred embodiment of the present invention, there is provided a compound of formula (Ia)

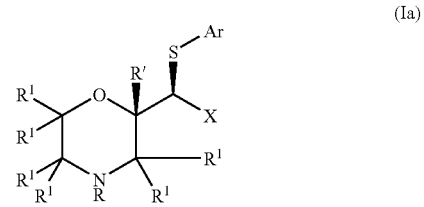

(Ia)

wherein:
R is H;
Ar is a phenyl group;
X is a phenyl group;
R' is H or $C_1$-$C_4$ alkyl;
each $R^1$ is independently H or $C_1$-$C_4$ alkyl; and pharmaceutically acceptable salts thereof.

In this further preferred embodiment, the group Ar may be substituted or unsubstituted phenyl. For example, Ar may be unsubstituted phenyl or, preferably phenyl substituted with 1, 2, 3, 4 or 5 substituents, preferably with 1 or 2, for example 1, substituent. When disubstituted, the substituted phenyl group is preferably substituted at the 2- and 5-positions When monosubstituted, the substituted phenyl group is preferably substituted in the 2-position. Suitable substituents include $C_1$-$C_4$ alkyl, O($C_1$-$C_4$ alkyl), S($C_1$-$C_4$ alkyl), halo, and phenyl optionally substituted with, for example, halo, $C_1$-$C_4$ alkyl, or O($C_1$-$C_4$ alkyl).

In this further preferred embodiment, the group X may be substituted or unsubstituted phenyl. For example, X may be phenyl substituted with 1, 2, 3, 4 or 5 substituents, preferably with 1 substituent. Suitable substituents include $C_1$-$C_4$ alkyl, O($C_1$-$C_4$ alkyl), and halo.

"$C_1$-$C_4$ alkyl" as used herein includes straight and branched chain alkyl groups of 1, 2, 3 or 4 carbon atoms, and may be unsubstituted or substituted. $C_1$-$C_2$ alkyl groups are preferred. Suitable substituents include halo. Thus the term "$C_1$-$C_4$ alkyl" includes haloalkyl. Similar terms defining different numbers of C atoms (e.g. "$C_1$-$C_3$ alkyl") take an analogous meaning. When R' is $C_1$-$C_4$ alkyl it is preferably unsubstituted. When $R^1$ is $C_1$-$C_4$ alkyl it is preferably unsubstituted.

"$C_3$-$C_6$ cycloalkyl" as used herein includes cyclopropyl, cyclobutyl, cyclopentyl and cyclohexyl.

"Halo" includes F, Cl, Br and I, and is preferably F or Cl.

"Pyridyl" as used herein includes 2-pyridyl, 3-pyridyl and 4-pyridyl.

"Thiophenyl" as used herein includes 2-thiophenyl and 3-thiophenyl.

For the compounds of formula (I) above, R' is preferably H or Me. More preferably R' is H.

For the compounds of formula (I) above, each $R^1$ is preferably H or Me with 0, 1, 2 or 3 of $R^1$ being Me. More preferably only 1 $R^1$ is Me. Most preferably all $R^1$ are H.

For the compounds of formula (I) above, it is preferred that R' and all $R^1$ are H.

A particularly preferred substituted $C_1$-$C_4$ alkyl group for the group Ar is trifluoromethyl.

A preferred group of compounds according to the present invention is represented by the formula (II);

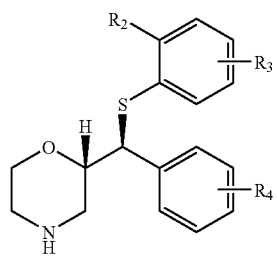

(II)

wherein

R$_2$ and R$_3$ are each independently selected from H, C$_1$-C$_4$ alkyl, O(C$_1$-C$_4$ alkyl), S(C$_1$-C$_4$ alkyl), halo and phenyl; and R$_4$ is selected from H and C$_1$-C$_4$ alkyl; and pharmaceutically acceptable salts thereof.

R$_2$ is preferably C$_1$-C$_3$ alkyl (especially trifluoromethyl), O(C$_1$-C$_3$ alkyl) (especially methoxy or trifluoromethoxy), F or Ph. R$_3$ is preferably H. R$_3$ is also preferably F. R$_4$ is preferably H.

Compounds of the present invention are selective inhibitors of norepinephrine reuptake. Biogenic amine transporters control the amount of biogenic amine neurotransmitters in the synaptic cleft. Inhibition of the respective transporter leads to a rise in the concentration of that neurotransmitter within the synaptic cleft. Compounds of Formula (I) and their pharmaceutically acceptable salts preferably exhibit a K$_i$ value less than 500 nM at the norepinephrine transporter as determined using the scintillation proximity assay as described below. More preferred compounds of Formula (I) and their pharmaceutically acceptable salts exhibit a K$_i$ value less than 100 nM at the norepinephrine transporter. More preferred compounds of Formula (I) and their pharmaceutically acceptable salts exhibit a K$_i$ value less than 50 nM at the norepinephrine transporter. Especially preferred compounds of Formula (I) and their pharmaceutically acceptable salts exhibit a K$_i$ value less than 20 nM at the norepinephrine transporter. Preferably, compounds of the present invention selectively inhibit the norepinephrine transporter relative to the serotonin and dopamine transporters by a factor of at least five, more preferably by a factor of at least ten. Advantageously, they have a reduced interaction (both as substrate and inhibitor) with the liver enzyme Cytochrome P450 (CYP2D6) compared with other norepinephrine-reuptake inhibitors, such as reboxetine. That is to say, they preferably exhibit less than 75% metabolism via the CYP2D6 pathway according to the CYP2D6 substrate assay described below and they preferably exhibit an IC50 of >6 μM according to the CYP2D6 inhibitor assay described below. They are indicated for the treatment of disorders associated with norepinephrine dysfunction in mammals, especially humans, including children, adolescents and adults.

The term "norepinephrine dysfunction" as used herein refers to a reduction in the amount of norepinephrine neurotransmitter within the synaptic cleft below that which would be considered to be normal. Thus the phrase "disorders associated with norepinephrine dysfunction in mammals" refers to disorders which are associated with a reduction in the amount of norepinephrine neurotransmitter within the synaptic cleft below that which would be considered to be normal for the mammalian species in question. Some examples of disorders currently believed to be associated with reduced levels of norepinephrine within the synaptic cleft are detailed below.

The compounds of the present invention are also indicated for the treatment of disorders which are ameliorated by an increase in the amount of norepinephrine neurotransmitter within the synaptic cleft of a mammal above that which would be considered to be normal for the mammalian species in question.

The term "treatment" as used herein refers to both curative and prophylactic treatment of disorders associated with norepinephrine dysfunction.

A compound of formula (IV) as described below may be prepared by reacting a compound of formula (III):

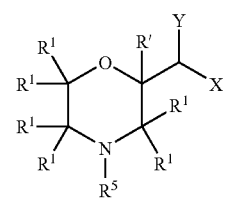

(III)

where R5 is a protecting group, e.g. benzyl, and X, R' and R$^1$ are as formula (I) above and Y is a leaving group, with an aryl thiol or hydroxy aryl compound. Examples of suitable leaving groups include halo and mesylate, but the nature of the leaving group is not critical.

Compounds of the present invention may also be prepared by deprotecting a compound of the formula (IV):

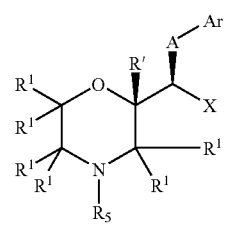

(IV)

where R$_5$ is a protecting group, e.g. benzyl, and A, Ar, X, R' and R$^1$ are as defined in formula (I) above to provide a compound of formula (I), optionally followed by the step of forming a pharmaceutically acceptable salt.

Suitable N-protecting groups will be known to the person skilled in the art as will methods for their removal. Further information on suitable deprotecting groups is contained in the well known text "Protective Groups in Organic Synthesis", Theodora W. Greene and Peter G. M. Wuts, John Wiley & Sons, Inc., New York, 1999, pp. 494-653. Preferred N-protecting groups include benzyl, allyl, carbamates such as benzyloxycarbonyl (cbz) and t-butyloxycarbonyl (boc) and amides.

For example, compounds of the present invention may be prepared by conventional organic chemistry techniques from N-benzyl-cyanomorpholine 1 (Route A) or N-benzyl-morpholinone 2 (Route B) as outlined in Scheme 1 below: For clarity, X is shown as phenyl and R' and R$^1$ are shown as H. It will be appreciated that analogous methods could be applied for other possible identities of X, R' and R$^1$.

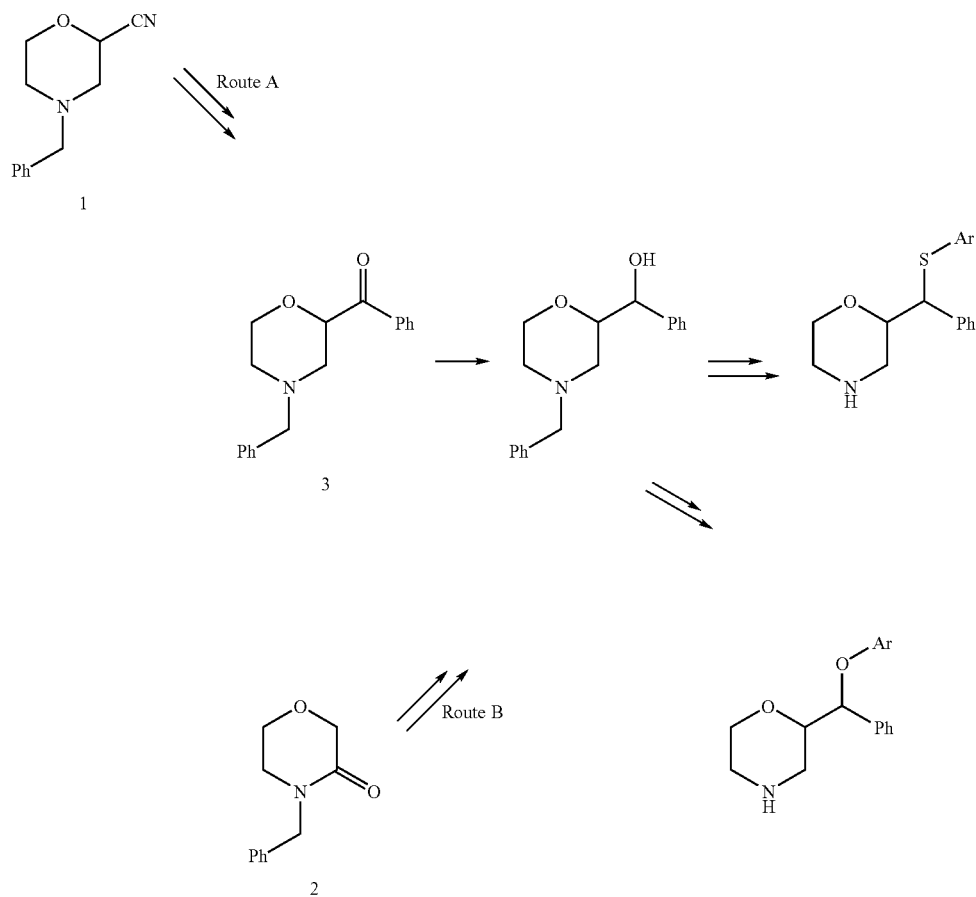
More detail of Route A is given in Scheme 2:
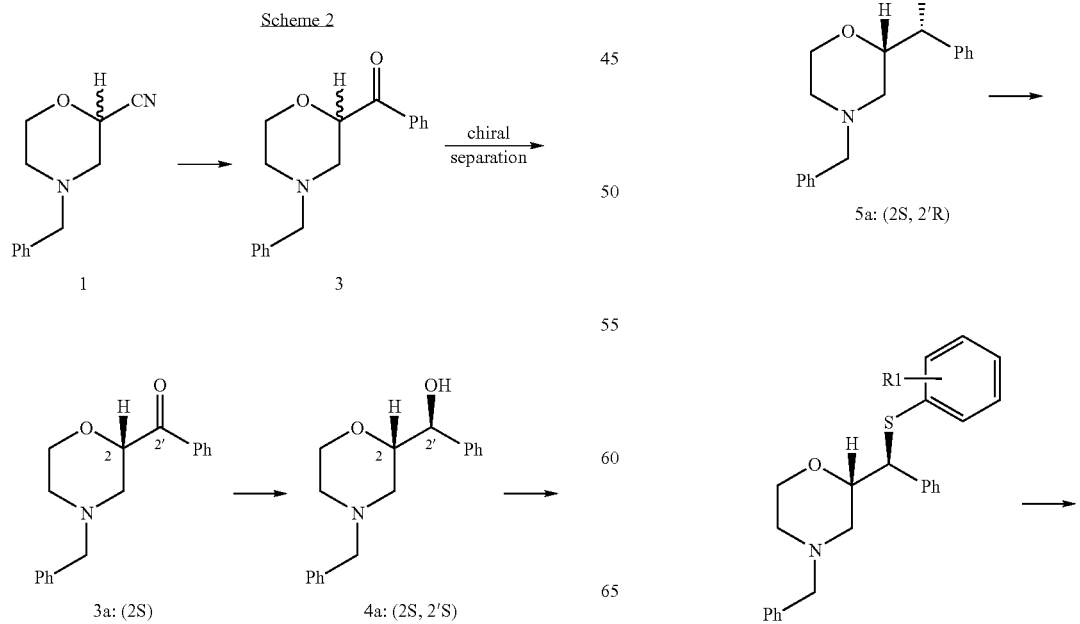

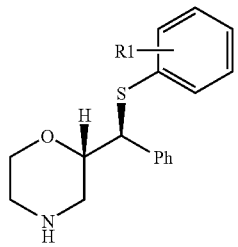

The amino alcohol 4a can be obtained by reaction of N-benzyl-cyanomorpholine 1 with a Grignard reagent, followed by acid hydrolysis to give racemic phenyl ketone 3 which may be separated on chiral HPLC. (2S)-Phenyl ketone 3a may then be reduced with DIP-Cl to give 4a in high diastereomeric excess. The amino alcohol 4a is converted into benzyl bromide 5a, to give the desired N-substituted aryl thio morpholines after displacement with the requisite aryl thiol. N-substituted aryloxy morpholines may be obtained in an analogous manner by displacement with the requisite hydroxyaryl compound. Alternatively, N-substituted aryloxy morpholines may be obtained by addition of a strong base, such as sodium hydride, to the amino alcohol 4a to form a nucleophilic alkoxide followed by an $S_NAr$ reaction with an Ar group substituted with a suitable leaving group (e.g. F). Deprotection of the tertiary amine gives the final products.

Detail of route B is given in Scheme 3:

outlined in Scheme 4. Amino alcohol pair 4c,4d may be converted into the corresponding mesylate. Displacement with the requisite thiol, followed by removal of the nitrogen protecting group furnishes aryl thiol morpholines as racemic mixtures of two diastereomers. The racemic aryl thiol morpholines may be separated into enantiomerically pure products using chiral HPLC technology. N-substituted aryloxy morpholines may be obtained in an analogous manner by displacement with the requisite hydroxyaryl compound.

Scheme 4

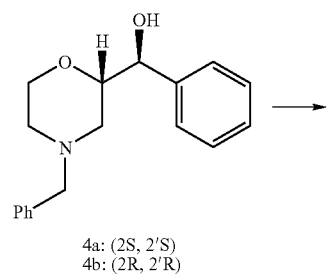

4a: (2S, 2'S)
4b: (2R, 2'R)

Scheme 3

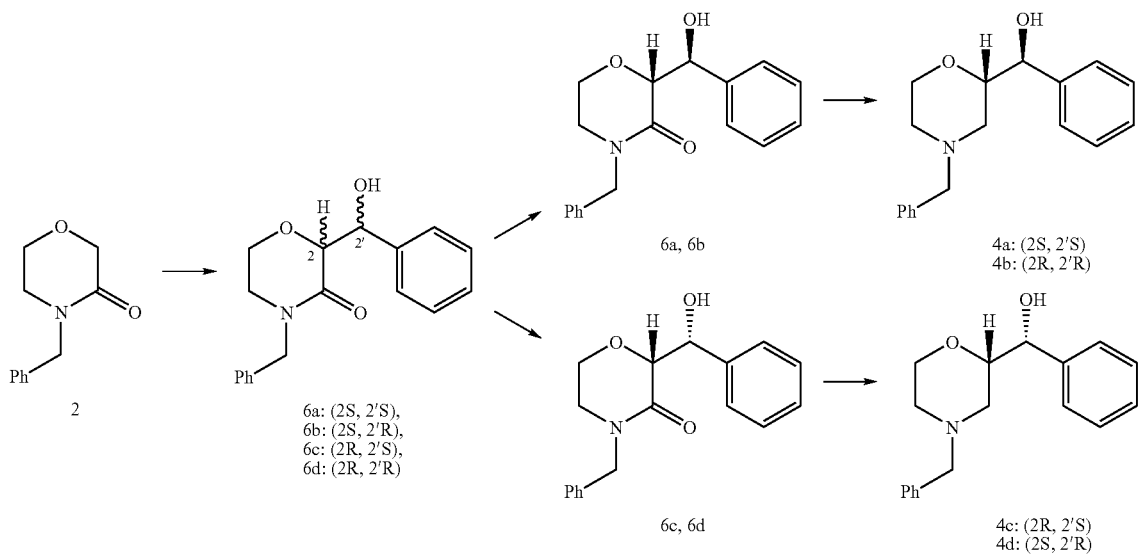

2

6a: (2S, 2'S),
6b: (2S, 2'R),
6c: (2R, 2'S),
6d: (2R, 2'R)

6a, 6b

4a: (2S, 2'S)
4b: (2R, 2'R)

6c, 6d

4c: (2R, 2'S)
4d: (2S, 2'R)

Treatment of N-benzyl morpholinone 2 with a strong base such as lithium diisopropylamide at low temperature followed by addition of benzaldehyde gives aldol adducts 6a-6d as a 2:1 mixture of diastereomer pairs 6a,6b and 6c,6d, which may be separated using conventional chromatographic techniques. Reduction with a borane reagent at elevated temperatures gives diasteremeric amino alcohol pairs 4a,4b and 4c,4d respectively.

Amino alcohol pair 4a,4b may be converted to bromide 5a,5b and further to racemic aryl thio morpholines as -continued

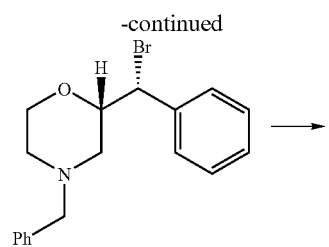

5a: (2S, 2'R)
5b: (2R, 2'S)

Aryl-substituted morpholines 33, 35, 37 may be obtained from morpholinone 2 as outlined in Scheme 5:
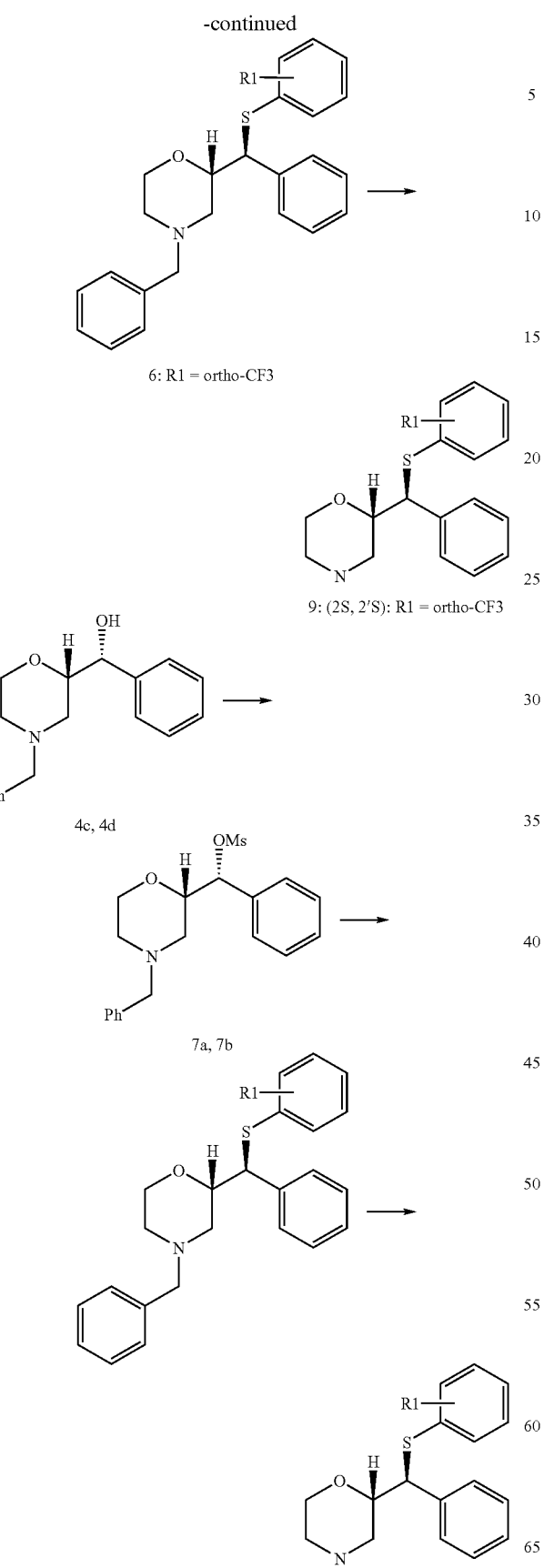
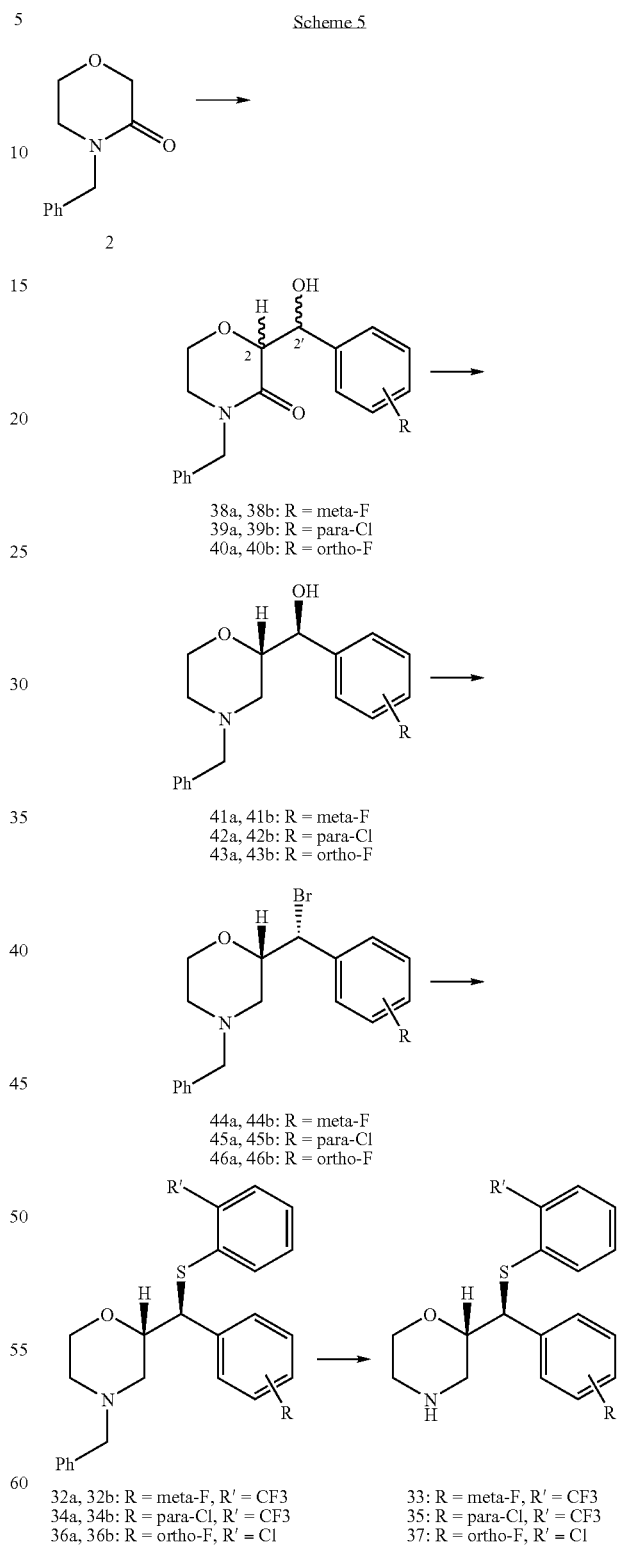
An alternative route to 9 is outlined in Scheme 6. This route makes use of a chiral auxiliary and gives 9 in enantiomerically pure form.

Scheme 6

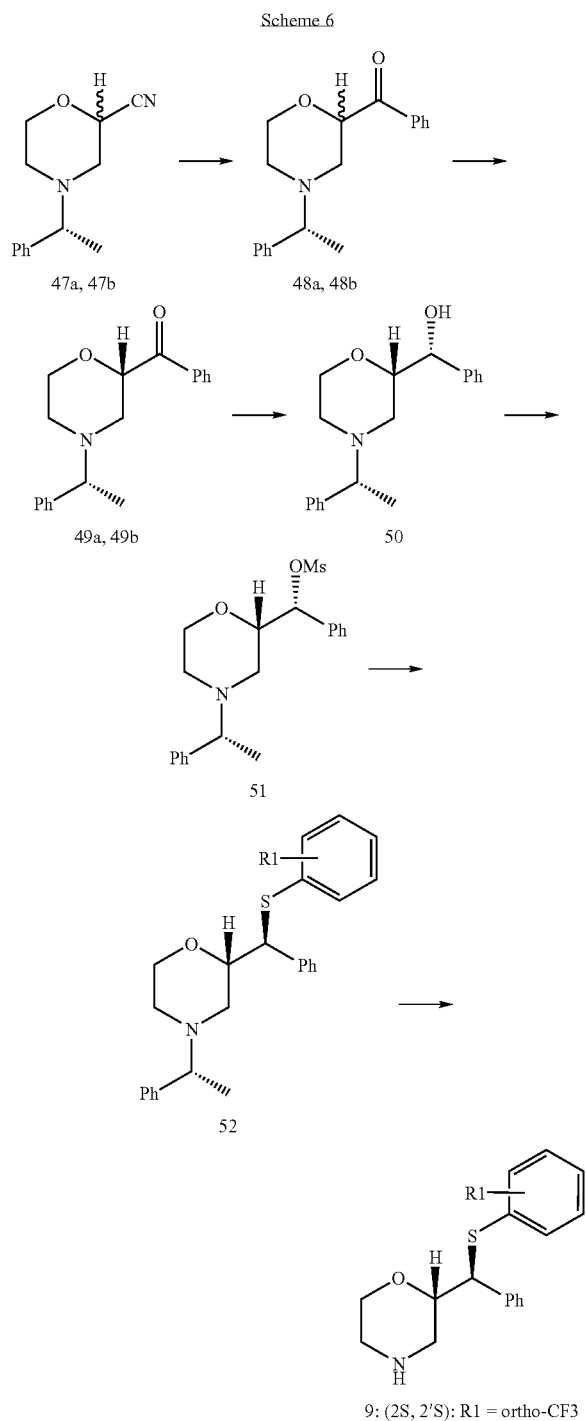

In addition to the compounds of formula I and formula II, and processes for the preparation of said compounds, the present invention further provides pharmaceutical compositions comprising a compound of formula I or formula II or a pharmaceutically acceptable salt thereof, together with a pharmaceutically acceptable diluent or carrier.

Further, the present invention provides a compound of formula I or formula II or a pharmaceutically acceptable salt thereof, for use as a pharmaceutical; and a compound of formula I or formula II or a pharmaceutically acceptable salt thereof, for use as a selective inhibitor of the reuptake of norepinephrine.

The present compounds and salts may be indicated for the treatment of disorders associated with norepinephrine dysfunction in mammals, including affective, anxiety, and cognitive disorders.

Disorders associated with norepinephrine dysfunction in mammals include, for example, nervous system conditions selected from the group consisting of an addictive disorder and withdrawal syndrome, an adjustment disorder (including depressed mood, anxiety, mixed anxiety and depressed mood, disturbance of conduct, and mixed disturbance of conduct and mood), an age-associated learning and mental disorder (including Alzheimer's disease), alcohol addiction, anorexia nervosa, apathy, an attention-deficit disorder (ADD) due to general medical conditions, attention-deficit hyperactivity disorder (ADHD) including the predominantly inattentive type of ADHD and the predominantly hyperactive-impulsive type of ADHD, bipolar disorder, bulimia nervosa, chronic fatigue syndrome, chronic or acute stress, cognitive disorders including mild cognitive impairment (MCI) and cognitive impairment associated with schizophrenia (CIAS), conduct disorder, cyclothymic disorder, dementia of the Alzheimers type (DAT), depression (including adolescent depression and minor depression), dysthymic disorder, emotional dysregulation, fibromyalgia and other somatoform disorders (including somatization disorder, conversion disorder, pain disorder, hypochondriasis, body dysmorphic disorder, undifferentiated somatoform disorder, and somatoform NOS), generalized anxiety disorder, hypotensive states including orthostatic hypotension, incontinence (i.e., stress incontinence, genuine stress incontinence, and mixed incontinence), an inhalation disorder, an intoxication disorder, mania, migraine headaches, neuropathic pain, nicotine addiction, obesity (i.e., reducing the weight of obese or overweight patients), obsessive compulsive disorders and related spectrum disorders, oppositional defiant disorder, pain including chronic pain, neuropathic pain and antinociceptive pain, panic disorder, peripheral neuropathy, post-traumatic stress disorder, premenstrual dysphoric disorder (i.e., premenstrual syndrome and late luteal phase dysphoric disorder), psoriasis, psychoactive substance use disorders, a psychotic disorder (including schizophrenia, schizoaffective and schizophreniform disorders), seasonal affective disorder, a sleep disorder (such as narcolepsy and enuresis), social phobia (including social anxiety disorder), a specific developmental disorder, selective serotonin reuptake inhibition (SSRI) "poop out" syndrome (i.e., wherein a patient who fails to maintain a satisfactory response to SSRI therapy after an initial period of satisfactory response), TIC disorders (e.g., Tourette's Disease), tobacco addiction and vascular dementia. The compounds of the present invention are particularly suitable for the treatment of attention deficit hyperactivity disorder, ADHD.

Thus, the present invention also provides a compound of formula I or formula II or a pharmaceutically acceptable salt thereof for selectively inhibiting the reuptake of norepinephrine. Preferably such selective inhibition occurs within mammalian cells (including mammalian cell membrane preparations), especially those found within the central and/or peripheral nervous system. More preferably such selective inhibition occurs within the cells of the central nervous system of a mammal, especially a human, in need thereof. The present invention also provides a compound of formula I or formula II or a pharmaceutically acceptable salt thereof for treating disorders associated with norepinephrine dysfunction in mammals; and the use of a compound of formula I or formula II, or a pharmaceutically acceptable salt thereof, in the manufacture of a medicament for selectively inhibiting the reuptake of norepinephrine; and the use of a compound of formula I or formula II, or a pharmaceutically acceptable salt thereof, in the manufacture of a medicament for the treatment of disorders associated with norepinephrine dysfunction in mammals, including the disorders listed herein.

Further, the present invention provides a method for selectively inhibiting the reuptake of norepinephrine in mammals, comprising administering to a patient in need thereof an effective amount of a compound of formula I or formula II or a pharmaceutically acceptable salt thereof; and a method for treating disorders associated with norepinephrine dysfunction in mammals, comprising administering to a patient in need thereof an effective amount of a compound of formula I or formula II or a pharmaceutically acceptable salt thereof.

The present invention includes the pharmaceutically acceptable salts of the compounds of formula I and formula II. Suitable salts include acid addition salts, including salts formed with inorganic acids, for example hydrochloric, hydrobromic, nitric, sulphuric or phosphoric acids, or with organic acids, such as organic carboxylic or organic sulphonic acids, for example, acetoxybenzoic, citric, glycolic, o-mandelic-1, mandelic-dl, mandelic d, maleic, mesotartaric monohydrate, hydroxymaleic, fumaric, lactobionic, malic, methanesulphonic, napsylic, naphtalenedisulfonic, naphtoic, oxalic, palmitic, phenylacetic, propionic, pyridyl hydroxy pyruvic, salicylic, stearic, succinic, sulphanilic, tartaric, 2-hydroxyethane sulphonic, toluene-p-sulphonic, and xinafoic acids.

In addition to the pharmaceutically acceptable salts, other salts are included in the invention. They may serve as intermediates in the purification of compounds or in the preparation of other, for example pharmaceutically acceptable, acid addition salts, or are useful for identification, characterisation or purification.

It will be appreciated that compounds of formula I and formula II possess one or more asymmetric carbon atoms, and that the present invention is directed specifically to individual stereoisomers. The particular stereochemistry of the present compounds is essential to the pharmacological profile of the compounds. In the present specification, where a structural formula does not specify the stereochemistry at one or more chiral centres, it encompasses all possible stereoisomers and all possible mixtures of stereoisomers (including, but not limited to, racemic mixtures), which may result from stereoisomerism at each of the one or more chiral centers.

The compounds of the present invention may be used as medicaments in human or veterinary medicine. The compounds may be administered by various routes, for example, by oral or rectal routes, topically or parenterally, for example by injection, and are usually employed in the form of a pharmaceutical composition.

Such compositions may be prepared by methods well known in the pharmaceutical art and normally comprise at least one active compound in association with a pharmaceutically acceptable diluent, excipient or carrier. In making the compositions of the present invention, the active ingredient will usually be mixed with a carrier or diluted by a carrier, and/or enclosed within a carrier which may, for example, be in the form of a capsule, sachet, paper or other container. Where the carrier serves as a diluent, it may be solid, semi-solid, or liquid material which acts as a vehicle, excipient or medium for the active ingredient. Thus, the composition may be in the form of tablets, lozenges, sachets, cachets, elixirs, suspensions, solutions, syrups, aerosols (as a solid or in a liquid medium), ointments containing, for example, up to 10% by weight of the active compound, soft and hard gelatin capsules, suppositories, injection solutions and suspensions and sterile packaged powders.

Some examples of suitable carriers are lactose, dextrose, vegetable oils, benzyl alcohols, alkylene glycols, polyethylene glycols, glycerol triacetate, gelatin, carbohydrates such as starch and petroleum jelly, sucrose sorbitol, mannitol, starches, gum acacia, calcium phosphate, alginates, tragacanth, gelatin, syrup, methyl cellulose, methyl- and propyl-hydrobenzoate, talc, magnesium stearate and mineral oil. The compounds of formula (I) can also be lyophilized and the lyophilizates obtained used, for example, for the production of injection preparations. The preparations indicated can be sterilized and/or can contain auxiliaries such as lubricants, preservatives, stabilizers and/or wetting agents, emulsifiers, salts for affecting the osmotic pressure, buffer substances, colourants, flavourings and/or one or more further active compounds, e.g. one or more vitamins. Compositions of the invention may be formulated so as to provide, quick, sustained or delayed release of the active ingredient after administration to the patient by employing procedures well known in the art.

The compositions are preferably formulated in a unit dosage form, each dosage unit containing from about 5 to about 500 mg, more usually about 25 to about 300 mg, of the active ingredient. The term "unit dosage form" refers to physically discrete units suitable as unitary doses for human subjects and other mammals, each unit containing a predetermined quantity of active material calculated to produce the desired therapeutic effect, in association with a suitable pharmaceutical carrier.

The following examples illustrate compounds of the present invention and methods for their preparation.

EXAMPLES

Stereochemical Conventions

The absolute stereochemistry of the following compound according to the present invention was determined as (2S, 2'S) using X-ray crystallography.

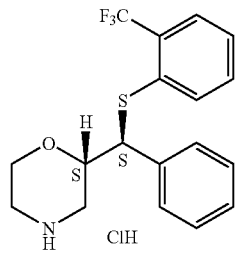

X-ray crystallographic data for the above compound is listed in Tables 1-6 herein.

All of the Examples herein were obtained as single isomers either through the use of chirally pure starting material or chiral separation methods, such as HPLC or fractional crystallization of salts formed from chiral acids/bases.

General Synthetic Procedures for the Preparation of Examples 1-17

The numbers included in the following Sections refer to the compounds illustrated on pages 7-10 herein.

General Procedure 1: Preparation of Racemic N-substituted Aryl Thiols

To a solution of 5a,5b (0.02 g, 0.52 mmol) and the requisite aryl thiol (1.1 eq) in anhydrous dimethylformamide (1 ml) at room temperature under nitrogen was added cesium carbonate (1.1 eq, 0.19 g, 0.57 mmol). The reaction mixture was heated to 95° C. for 2 hours. The reaction mixture was allowed to cool to room temperature, diluted with ethyl acetate, then washed sequentially with water, brine, dried over magnesium sulphate and finally concentrated in vacuo.

General Procedure 2a: Deprotection of N-substituted Aryl Thiols

To a solution of the requisite N-benzyl aryl thiol in anhydrous dichloromethane (5 ml) was added solid supported Hünig's base (Argonaut, 3.56 mmol/g, 2 eq) and α-chloroethyl chloroformate (3 to 10 eq) at room temperature under nitrogen. The reaction mixture was heated to 40° C. and followed by LCMS analysis. After completion the reaction mixture was filtered, and the resin washed with dichloromethane. The combined organic phases were concentrated in vacuo. Methanol (HPLC grade, 25 ml) was added and the solution heated to 60° C. for 1.5 to 4 hours. After complete consumption of starting material the methanol solution was evaporated to give a solid which was further purified as detailed for individual compounds.

General Procedure 2b: Deprotection of N-substituted Aryl Thiols

To a solution of the requisite N-benzyl aryl thiol (1 eq) in ethyl acetate at room temperature was added phenylchloroformate (3 eq). The mixture was warmed under reflux for 2 hours. The mixture was then cooled to room temperature and 30% NaOH with water was added over 1 hour. The biphasic system was stirred for 1.5 hours at room temperature and the organic layer was separated. The organic layer was washed with water, dried over MgSO$_4$, filtered and rinsed with ethyl acetate.

To the mixture of carbamate and benzylchloride in ethyl acetate was added 5.6M dimethylamine in ethanol. The solution was warmed under reflux (70-72° C.) for 2 hours. After cooling at room temperature, water and 12N HCl were added and the mixture was stirred for 10 minutes. The layers were separated and the organic phase was washed twice with water. Then the organic layer was concentrated (T=50° C.) until crystallization. MeOH was added and approx. 40% of solvent was then removed under reduce pressure, this operation was repeated. The heterogeneous mixture was stirred for 0.5 hours at room temperature and filtered. The precipitate was washed twice with MeOH and dried under reduce pressure at 40° C. to yield the carbamate.

To a biphasic mixture of 30% NaOH and isopropanol warmed to 65° C., was added the carbamate. The heterogeneous mixture was warmed under reflux for 4 hours and then cooled to room temperature and post-agitated overnight. The organic layer was concentrated under reduce pressure and the yellow solid obtained was added to a mixture of AcOEt and 1N NaOH. After separation of the layers, the organic one was washed with 1N NaOH. The aqueous layers were combined and extracted with AcOEt. The combined organic layers were dried over MgSO$_4$, filtered and concentrated under reduce pressure to dryness to obtain the free amine.

General Procedure 3: Conversion of Amines into Hydrochloride Salts

To a solution of the requisite amine in dry diethyl ether (1 ml) was added hydrochloric acid (500 μl of a 1M solution in diethyl ether). A white precipitate immediately formed. The suspension was then sonicated for 5 minutes. Ether was blown off with a stream of nitrogen and the samples were dried under high vacuum for several hours to give the hydrochloride salts in near quantitative yield as white solids.

General Procedure 4: Aldoladdition with Substituted Benzaldehydes

Preparation of 38a,38b; 39a,39b; 40a,40b

N-Benzylmorpholinone (1.0 eq) and the requisite aldehyde (1.1 eq) were dissolved in anhydrous tetrahydrofuran (25 ml) under nitrogen and the reaction cooled to −78° C. Then, lithium diisopropylamide (1.1 eq of a 2M solution in heptane/tetrahydrofuran/ethylbenzene) was added over approximately 20 minutes, whilst maintaining the reaction temperature below −78° C. The resulting yellow solution was stirred at −78° C. for 1 hour and then allowed to warm to room temperature. The reaction was quenched with saturated ammonium chloride solution (25 ml) and extracted into ethyl acetate. The combined organic layers were dried with magnesium sulphate, filtered and concentrated in vacuo, to give a yellow oil which was purified by column chromatography on silica gel (eluent: ethyl acetate/hexane 70/100 [v/v]).

General Procedure 5: Reduction of Substituted Aldol Adducts

Preparation of 41a,41b; 42a,42b; 43a,43b

To a solution of the requisite amide 38a,38b, 39a,39b or 40a,40b (1.1 mmol) in anhydrous tetrahydrofuran under nitrogen at room temperature was slowly added borane (4 eq of a 1M solution in tetrahydrofuran). The solution was stirred at 60° C. for 2 hours. The reaction was cooled to room temperature; dry methanol (excess) was slowly added, followed by aqueous hydrochloric acid solution (1M, excess). The reaction mixture was heated to 60° C. for 1 hour and quenched with aqueous potassium carbonate solution (1M, excess) and extracted with diethyl ether. The combined organic layers were washed with brine, dried with magnesium sulphate, filtered and concentrated in vacuo yielding a yellow oil which was purified by column chromatography on silica gel (eluent: ethyl acetate/hexane 10/100 [v/v]).

Preparation of Intermediates for the Synthesis of Examples 1-17

4-Benzylmorpholin-3-one (2)

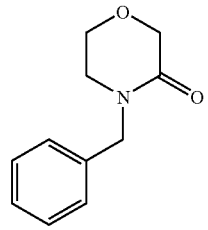

A solution of N-benzyl-N-(2-hydroxyethyl) chloroacetamide (627.7 g, 2.76 mol) in tert-butanol (0.9 l) was stirred under nitrogen while warming to 25-30° C. Potassium tert-butoxide (2.897 l of a 1M solution in tert-butanol, 2.90 mol, 1.05 eq) was added over 2 hours. The reaction mixture was then stirred at room temperature for 90 minutes. Ice-cold water (6 l) was added and the resultant cloudy solution extracted with ethyl acetate. The combined organic layers were washed with brine, dried over magnesium sulphate and evaporated in vacuo to give a light brown oil (441 g, 84%), which was used in the next stage without further purification; MW 191.23; $C_{11}H_{13}NO_2$; $^1$H NMR (CDCl$_3$): 7.29-7.40 (5H, m), 4.67 (2H, s), 4.28 (2H, s), 3.87 (2H, t, 5 Hz), 3.31 (2H, t, 5 Hz); LCMS: (12 min method) m/z 192 [M+H]+ @ Rt 1.00 min.

4-Benzyl-morpholine-2-carbonitrile (1)

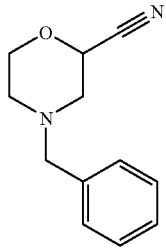

A one-litre reactor with mechanical stirring, cooled by an ice bath, was charged with N-benzylethanolamine (172.2 g; 1 equiv. available from Aldrich Chemical Company). 2-Chloroacrylonitrile (100 g; 1 equiv. available from Aldrich Chemical Company) was added dropwise over 2 minutes. The temperature was maintained between 23° C. and 29° C. by means of the ice bath and subsequently a water bath at 15° C. N-Benzylethanolamine was still detected on TLC after 4.5 h stirring. After one night stirring at room temperature (water bath), no N-benzylethanolamine was detectable by $^1$H NMR. The mixture was dissolved in tetrahydrofuran and transferred to a 2 L reactor cooled to −5° C. by ice/NaCl bath. The total volume of tetrahydrofuran was 1.35 L. Potassium tert-butoxide (148 g; 1.1 equiv.) was added by portions in 1 hour, keeping the reaction temperature at 0±2° C. After 1 hour post-stirring at 0° C., the mixture was quenched with saturated NaHCO$_3$ (500 mL). The aqueous layer was extracted with diethyl ether (500 mL). Organic layers were dried on MgSO$_4$ and evaporated to dryness. The title compound (149.8 g; 65%) was obtained after percolation of the 250 g dry residue on 1 kg of SiO$_2$, eluting with the following gradient:

| | |
|---|---|
| 5% AcOEt-95% n-heptane | 2.5 L |
| 10% AcOEt-90% n-heptane | 2 L |
| 15% AcOEt-85% n-heptane | 2 L |
| 20% AcOEt-80% n-heptane | 5 L |

(2S)-(4-Benzyl-morpholin-2-yl)-phenyl-methanone (3a) and (2R)-(4-Benzyl-morpholin-2-yl)-phenyl-methanone (3b) Preparation via Route A in Scheme 1

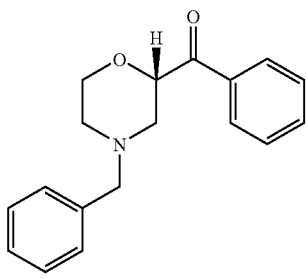

A 3 l double jacket reactor was charged with 1 (135.05 g; 1 eq) (obtained by the method above or by the method disclosed in King, F. K.; Hadley, M. S.; Joiner, K. T.; Martin, R. T.; Sanger, G. J.; Smith, D. M.; Smith, G. E.; Smith, P.; Turner, D. H.; Watts, E. A., J. Med. Chem. 1993, 36(6), 683.) and dry diethyl ether (1.4 l). Alternatively, toluene may be used in place of diethyl ether. When Tj=0° C. and Tm=1° C. (Tj=temperature of the jacket, Tm=temperature of the mass), phenyl magnesium chloride (2M sol. in tetrahydrofuran, 360 ml, 1.08 equiv., available from Aldrich Chemical Company) was added dropwise over 1 hour. Tm rose to 4° C. and came back to 2° C. at the end of the addition. Tm was progressively raised to 17.5° C. within 45 minutes and the mixture stirred at this temperature for another 45 minutes. The reactor was cooled down to Tm=2° C. and Tj=0° C. (75 minutes) and hydrochloric acid (700 ml of 5N solution) was added in two portions. Tm rose to 33° C. After some minutes, the hydrochloride salt of the ketone crystallised. When Tm=Tj=room temperature, the triphasic suspension was filtered. The organic layer of the mother liquors, which contains impurities, was eliminated. The filtration cake was then washed with methylene chloride (700 ml). This liquor was charged in the reactor with the acid aqueous layer. Treatment of the hydrochloride salt: After drying under vacuum, 164.4 g of the hydrochloride contaminated with MgCl$_2$ were suspended in a biphasic mixture of water/methylenechloride (500 ml/800 ml). The suspension was basified with aqueous sodium hydroxide (75 ml of a 30% solution) under ice bath cooling. Mg(OH)$_2$ precipitated and the aqueous layer was extracted with methylene chloride. The organic layers are filtered on a bed of Celite 512 after adding some Celite to the layers themselves. The filtered organic phase was dried over magnesium sulphate and evaporated to dryness. The ketone crystallizes readily on standing (132.4 g; 70%). Treatment of the mother liquors: The combined organic phases were washed with aqueous sodium hydroxide (750 ml of a 2N solution). Celite 512 (160 g) was added to the suspension which was then filtrated through a bed of Celite. The aqueous layer was separated and extracted with methylene chloride. The combined organic phases were dried over magnesium sulphate and evaporated to dryness to provide 35.8 g of 3a,3b enriched with unreacted nitrile. Compound 3a was obtained after separation using chiral HPLC on a Daicel chiralpak AD 20 µm column with 100% Ethanol/0.3% DMEA as eluent at a flow rate of 150 ml/min and UV-detection at 300 nm. Alternatively, the two enantiomers may be separated by fractional crystallization from acetonitrile using from 0.55 to 1 equivalent of dibenzoyltartaric acid to generate diastereoisomeric salts of the title compound. The crystals may be collected by filtration and neutralized with 30% NaOH to afford the optically enriched title compound.

(2S)-(4-Benzyl-morpholin-2-yl)-phenyl-methanone (3a) and (2R)-(4-Benzyl-morpholin-2-yl)-phenyl-methanone (3b)—One Pot Synthesis A 1600 L GL reactor under N$_2$ was successively loaded with 2-chloroacrylonitrile (33.2 kg, 379 moles) and toluene (114 L) at 21° C. Then, N-benzylethanolamine (57 kg, 377 moles) was added and the reaction mixture was post-agitated at room temperature for about 17 h. Then, the mixture was diluted with toluene (336 L), cooled down to −12.4° C. and potassium t-butoxide (42.3 kg, 377 moles) was added in portions (10) maintaining −13.7° C.≦Tmass≦−2.8° C. The mixture was post-agitated at about 0° C. for 2.5 h, quenched by adding ultra pure water (142.5 L) maintaining 2.1° C.≦Tmass≦8.7° C. The aqueous layer (176 kg) was separated after 35 minutes of post-stirring allowing the mixture to reach 15° C. and the toluene layer was washed with ultra pure water (142.5 L) and the aqueous layer (162 kg) was separated. The organic layer was then concentrated under reduced pressure (150 mbars) maintaining Tmass≦60° C. in order to distill 162 kg of toluene. The filtrates were then diluted with toluene (114 L) and treated with SiO$_2$ (Merck silica gel 60, 0.063-0.1 mm, 74.1 kg) under agitation at room temperature for 1.25 h. SiO$_2$ was filtered and rinsed with toluene (2×114 L). Then, the filtrates were concentrated under reduced pressure (150 mbars) maintaining Tmass≦60° C. in order to distill 351.8 kg of toluene (KF: 0.01% w/w H$_2$O).

The solution of 4-Benzyl-morpholine-2-carbonitrile (169.2 kg) was diluted with toluene (157 L) and was cooled to 0° C. and phenylmagnesiumchloride (25 wt. % solution in THF, 213 kg, 389 moles, 1.36 molar equiv.) was slowly added (over 3.5 h) to the reaction mixture, maintaining the temperature at −3° C.≦Tmass≦7° C. The reaction mixture was post-stirred for 2 hours at Tmass≈0° C. Then, the quench was performed by adding acetic acid (8.55 L, Tmass=5→17.2° C.), post stirring 10 minutes and cooling to 5° C. before adding an acetic acid/water mixture (229 L, 33/67 v/v). During the quench, addition was performed at such a rate that Tmass did not exceed 20° C. (typical Tmass=4.6° C. to 10.4° C.). The mixture was post-agitated overnight at RT and the aqueous layer (285.8 kg) was extracted.

The toluene layer was cooled to 0° C. and a 5 N NaOH aqueous solution (420.1 kg) was slowly added maintaining the temperature at −2.4° C.≦Tmass≦11° C. The reaction mixture was post-stirred for 1 h and the aqueous layer (494.8 kg) was extracted. The toluene layer was concentrated under reduced pressure (50 mbars) maintaining Tmass≦60° C. in order to distill 356.2 kg of toluene and isopropanol (180.4 kg) was added. The toluene was stripped off under reduced pressure (100 mbars) maintaining Tmass≦60° C. in order to distill 186.4 kg of toluene and isopropanol (135 kg) was added again to the mixture. A last distillation of toluene was performed under reduced pressure (50 mbars) maintaining Tmass≦60° C. in order to distill 131 kg of toluene and isopropanol (49.4 kg) was finally added to the mixture and the solution was stirred at RT until crystallization (17 minutes).

Ultra pure water was added (125.4 L) and the mixture was stirred overnight at RT and cooled down to about 0° C. for 1 hour. The precipitate was filtered and rinsed with a cooled water/isopropanol 50/50 v/v solution (76.6 kg). The wet precipitate was dried under vacuum at Tjack=35° C. for 96 hours to obtain the title compound as an off-white powder with 59% overall yield. The title compound may be resolved by the fractional crystallisation process described above.

(S)-Phenyl[(2S)-4-(phenylmethyl)morpholin-2-yl] methanol (4a)

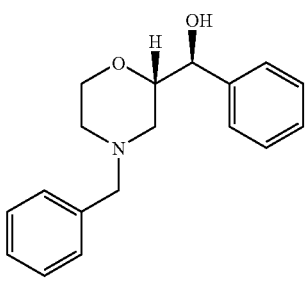

To a stirred solution of [(−)-B-chlorodisopinocampheylborane] (45 g, 140 mmol) in dry tetrahydrofuran (300 ml) under nitrogen was added 3a (7.97 g, 28.4 mmol) in one portion. The reaction mixture was stirred at room temperature for 18 hours. The mixture was evaporated in vacuo and extracted from 2M aqueous sodium hydroxide solution into ethyl acetate. The combined organic extracts were washed with brine, dried, filtered and evaporated. The crude product was taken up in chloroform/methanol (1:1 [v/v]) and absorbed onto 150 g SCX-2 ion exchange resin. After elution of borane residues with methanol the product was eluted with 2M ammonia in methanol. Removal of solvent in vacuo yielded the product as yellow oil. This was further purified by flash chromatography (eluent: ethyl acetate/isohexane 80/20 [v/v]). After removal of solvents, the product crystallised on standing (6.73 g, 84%); MW 283.37; $C_{18}H_{21}NO_2$; $^1$H NMR (CDCl$_3$): 7.32-7.45 (10H, m), 4.67 (1H, d, 7 Hz), 4.03 (1H, dt, 11 Hz and 2 Hz), 3.86-3.73 (2H, m), 3.64 (1H, d, 13 Hz), 3.39 (1H, d, 13 Hz), 3.30 (1H, br, s), 2.68 (1H, d, 12 Hz), 2.56 (1H, d, 10 Hz), 2.28-2.15 (2H, m); LCMS: m/z 284 [M+H]+ @ Rt 0.95 min.

(2S)-2-[(R)-bromo(phenyl)methyl]-4-(phenylmethyl) morpholine (5a)

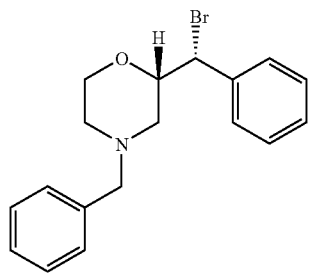

To a solution of 4a (4.71 g, 16.6 mmol) in anhydrous chloroform (200 ml) under nitrogen was added triphenylphosphine dibromide (14.04 g, 33.26 mmol). The reaction mixture was heated at 60° C. overnight. The mixture was allowed to cool to room temperature then washed with saturated aqueous sodium carbonate solution, dried over sodium sulphate and concentrated in vacuo. The resulting residue was purified by flash chromatography on silica (eluent: ethyl acetate/isohexane gradient 10/90 to 30/70 [v/v]) to give 5a as a white solid (4.63 g, 81%); MW 346.27; $C_{18}H_{20}BrNO$; $^1$H NMR (CDCl$_3$): 7.14-7.39 (10H, m), 4.83 (1H, d, 7 Hz), 4.01 (1H, br, t, 8 Hz), 3.73 (1H, br, d, 11 Hz), 3.60-3.48 (2H, m), 3.39 (1H, d, 12 Hz), 3.20 (1H, d, 11 Hz), 2.50 (1H, d, 10 Hz), 2.07 (2H, t, 10 Hz); LCMS: (6 min method) m/z 346 [M]+ @ Rt 2.51 min.

(2S)-2-[(S)-Hydroxy(phenyl)methyl]-4-(phenylmethyl)morpholin-3-one (6a)

and (2S)-2-[(R)-Hydroxy(phenyl)methyl]-4-(phenylmethyl)morpholin-3-one (6b)

and (2R)-2-[(S)-Hydroxy(phenyl)methyl]-4-(phenylmethyl)morpholin-3-one (6c)

and (2R)-2-[(R)-Hydroxy(phenyl)methyl]-4-(phenylmethyl)morpholin-3-one (6d)

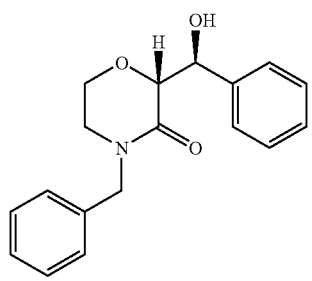

-continued

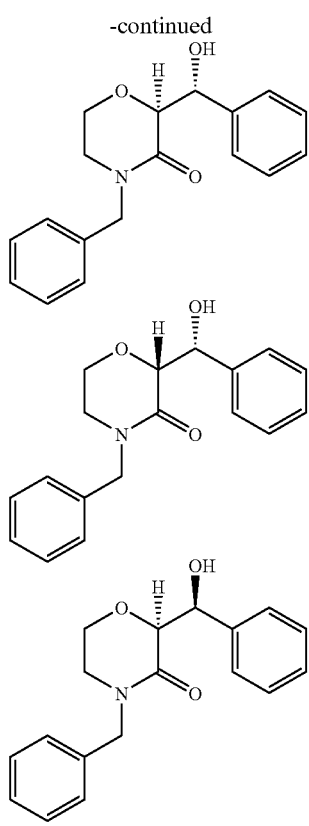

To a stirred solution of 2 (5.02 g, 26 mmol) in anhydrous tetrahydrofuran (25 ml) under nitrogen at −78° C. was added lithium diisopropylamide (1.5 eq, 39 mmol, 19.5 ml of a 2M solution in heptane/tetrahydrofuran/ethylbenzene) over approximately 20 minutes, whilst maintaining the reaction temperature below −75° C. The resulting brown solution was stirred for a further 30 minutes at −78° C., before being added over approximately 30 minutes to a solution of benzaldehyde (1.2 eq, 3.29 g, 31 mmol) in anhydrous tetrahydrofuran (15 ml) under nitrogen at −78° C., whilst again maintaining the reaction temperature below −75° C. The resulting yellow solution was stirred at −78° C. for 1 hour, before being allowed to warm to room temperature slowly over 1 hour. The reaction mixture was cautiously quenched by addition of saturated ammonium chloride solution (50 ml) and the tetrahydrofuran was evaporated in vacuo. The resulting cloudy aqueous solution was extracted with dichloromethane, and the organic extracts were combined, washed with brine, dried over sodium sulphate and the dichloromethane evaporated in vacuo to give a thick brown oil (9.2 g), which partially crystallised on standing. After purification by flash column chromatography (eluent: ethyl acetate/dichloromethane 10/90 to 20/80 gradient [v/v]) 6a,6b was obtained as light red crystals (2.46 g, 32%); MW 297.36; $C_{18}H_{19}NO_3$; $^1$H NMR (CDCl$_3$): 7.36-7.41 (2H, m), 7.16-7.31 (6H, m), 6.86-6.91 (2H, m), 5.14 (1H, d, 33 Hz), 4.71 (1H,d, 14 Hz), 4.48 (1H, d, J 3 Hz), 4.25 (1H, d, 14 Hz), 4.20 (1H, br, s), 3.89 (1H, ddd, 12 Hz, 3 Hz, 2 Hz), 3.67 (1H, dt, 11 Hz, 3 Hz), 3.16 (1H, dt, 12 Hz and 4 Hz), 2.86 (1H, br, d, 12 Hz); LCMS: m/z 298 [M+H]+ @ Rt 1.24 min. 6c, 6d was isolated as a brown solid (1.42 g) contaminated with 2. Trituration with ethyl acetate afforded pure 6c,6d as a white solid (0.484 g, 6%); MW 297.36; $C_{18}H_{19}NO_3$; $^1$H NMR (CDCl$_3$): 7.55-7.61 (2H, m), 7.36-7.50 (6H, m), 7.25-7.31 (2H, m), 5.21 (1H, d, 2 Hz), 5.09 (1H, d, J 7 Hz and 2 Hz), 4.73 (2H, s), 4.37 (1H, d, J 8 Hz), 4.01 (1H, ddd, 12 Hz, 3 Hz, 2 Hz), 3.77 (1H, dt, 11 Hz, 4 Hz), 3.50 (1H, dt, 12 Hz, 4 Hz), 3.16 (1H, br, d, 12 Hz); LCMS: m/z 298 [M+H]+ @ Rt 1.24 min.

(S)-Phenyl[(2S)-4-(phenylmethyl)morpholin-2-yl]methanol (4a)

and (R)-Phenyl[(2R)-4-(phenylmethyl)morpholin-2-yl]methanol (4b)

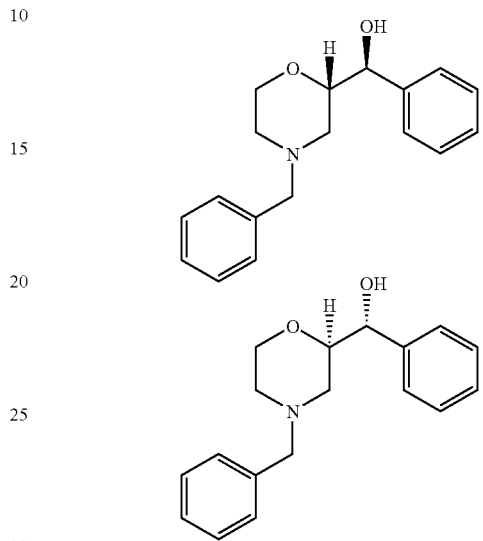

To a solution of 6a,6b (0.033 g, 1.1 mmol) in anhydrous THF (5 ml) under nitrogen at room temperature was slowly added borane (4 eq, 4.4 ml of a 1M solution in tetrahydrofuran, 4.4 mmol). The solution was stirred at 60° C. for 2 hours. After cooling down to room temperature, dry methanol (2 ml) was slowly added to quench excess borane reagent. After addition of aqueous hydrochloric acid solution (2 ml of a 1M solution) the reaction mixture was heated to 60° C. for 1 hour. The organic solvents were evaporated in vacuo and the concentrated solution was poured onto aqueous potassium carbonate solution (10 ml of a 1M solution) and extracted with diethyl ether (2×20 ml). The combined organic layers were washed with brine, water, dried over magnesium sulphate and concentrated in vacuo. Purification by flash column chromatography (eluent: hexane/ethyl acetate/triethylamine 90/9/1 [v/v/v]) gave a viscous oil (0.19 g, 60%); MW 283.37; $C_{18}H_{21}NO_2$; $^1$H NMR (CDCl3): 7.45-7.32 (10H, m), 4.67 (1H, d, 7 Hz), 4.03 (1H, dt, 11 Hz, 2.7 Hz), 3.86-3.73 (2H, m), 3.64 (1H, d, 13 Hz), 3.39 (1H, d, 13 Hz), 3.30 (1H, br, s), 2.68 (1H, d, 13 Hz), 2.56 (1H, d, 11 Hz), 2.28-2.15 (2H, m); LCMS: m/z 284 [M+H]+ @ Rt 0.95 min.

(R)-[(2S)-4-Benzylmorpholinyl](phenyl)methanol (4c)

and (S)-[(2R)-4-Benzylmorpholinyl](phenyl)methanol (4d)

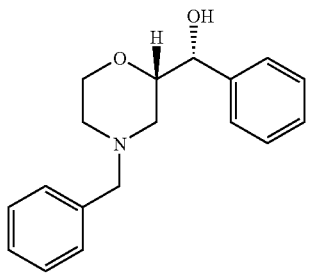

-continued

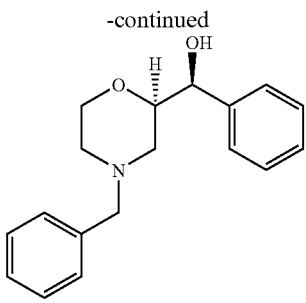

Using the procedure described for the preparation of 4a,4b starting from 6c,6d (0.14 g, 0.45 mmol) 4c,4d was obtained as a viscous oil (0.098 g, 68%); MW 283.37; $C_{18}H_{21}NO_2$; $^1$H NMR (CDCl$_3$): 7.17-7.28 (10H, m), 4.80 (1H, d, 4 Hz), 3.88 (1H, dt, 11 Hz, 3 Hz), 3.72 (1H, m), 3.61-3.68 (1H, m), 3.50 (1H, d, 13 Hz), 3.25 (1H, d, 13 Hz), 2.52 (2H, br, t, 12 Hz), 2.17 (1H, t, 11 Hz), 2.08 (1H, td, 11 Hz, 3 Hz); LCMS: m/z 284 [M+H]+ @ Rt 0.98 min.

(2S)-2-[(R)-Bromo(phenyl)methyl]-4-phenylmethyl) morpholine (5a)

and (2R)-2-[(S)-Bromo(phenyl)methyl]-4-(phenylmethyl)morpholine (5b)

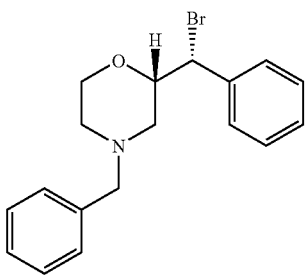

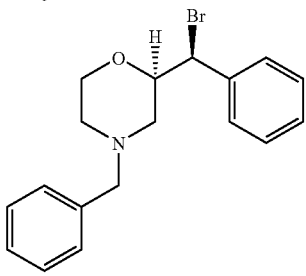

To a solution of 4a,4b (10.27 g, 36.29 mmol) in anhydrous dichloromethane (150 ml) under nitrogen at room temperature was added freshly recrystallised triphenylphosphine (13.32 g, 50.80 mmol, 1.4 eq) followed by carbon tetrabromide (16.85 g, 50.8 mmol, 1.4 eq) as a solution in anhydrous dichloromethane (50 ml). After 15 minutes the reaction mixture was diluted with dichloromethane (100 ml) and washed with saturated aqueous solution of sodium hydrogencarbonate, brine, dried over magnesium sulphate and concentrated in vacuo to give an orange oil (42.0 g). To the orange oil was added diethyl ether (200 ml) and the resulting suspension was sonicated for 30 minutes. The solvent was decanted and the process repeated with a further portion of diethyl ether. The combined organic extracts were concentrated in vacuo to yield an orange solid (22.0 g) which was purified by flash column chromatography (eluent: ethyl acetate/hexane/triethylamine 10/89.5/0.5 [v/v/v]) 5a,5b was otained as a white solid (7.20 g, 57%). Alternative Work-up: The reaction mixture was poured onto a silica (160 g) filtration pad which was washed with dichloromethane (14× 250 ml). After removal of solvents in vacuo and purification by flash column chromatography (eluent: ethyl acetate/hexane/triethylamine gradient 5/94.5/0.5 to 10/89.5/0.5 [v/v/v]) to give a white solid (6.05 g, 48%); MW 346.27; $C_{18}H_{20}BrNO$; $^1$H NMR (CDCl$_3$): 7.14-7.39 (10H, m), 4.83 (1H, d, 7 Hz), 4.01 (1H, br, t, 8 Hz), 3.73 (1H, br, d, 11 Hz), 3.48-3.60 (2H, m), 3.39 (1H, d, 12 Hz), 3.20 (1H, d, 11 Hz), 2.50 (1H, d, 10 Hz), 2.07 (2H, t, 11 Hz); LCMS: m/z 348/346 [M+H]+ @ Rt 1.20 min.

4-[(1R)-1-Phenylethyl]morpholine-(2S)-carbonitrile (47a)

and

4-[(1R)-1-Phenylethyl]morpholine-(2R)-carbonitrile (47b)

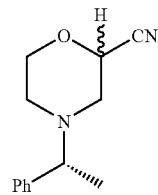

To (R)-(−)-2-hydroxyethyl-α-phenethylamine (1.65 g, 10.0 mmol) in diethyl ether (10 ml) was added at room temperature 2-chloroacrylonitrile (0.80 ml, 10.0 mmol) with stirring. The mixture was stirred at room temperature for 4.5 days when additional 2-chloroacrylonitrile (0.8 ml, 10.0 mmol) was added. After stirring another 3.5 days, the reaction mixture was concentrated in vacuo to give an oil. The oil was dissolved in dry tetrahydrofuran (30 ml), cooled under nitrogen to 0° C. and potassium tert-butoxide (1.23 g, 11.0 mmol) added. The solution was stirred at 0° C. for 2 hours then at reflux for 1.5 hours, cooled, diluted with diethyl ether and washed with aqueous saturated sodium bicarbonate. The organic phase was extracted with 2N hydrochloric acid and the aqueous made basic by addition of solid sodium bicarbonate and extracted with diethyl ether. The organic phase was dried over magnesium sulphate, filtered and evaporated to a brown oil. The crude product was purified by flash chromatography (eluent: ethyl acetate/hexane gradient 100% ethyl acetate to 50/50 [v/v]) to give 47a,47b as a colourless oil (0.58 g, 27%%); MW 216.29; $C_{13}H_{16}N_2O$; $^1$H NMR (CDCl$_3$) 7.25-7.38 (5H, m), 4.6 (1H, dd), 4.54 (1H, dd), 3.91-4.06 (2H, m), 3.66-3.82 (2H, m), 3.39-3.49 (2H, m), 2.30-2.89 (4H, m), 1.39 (3H, d). m/z [M+H]$^+$ 217.

Phenyl{(2S)-4-[(1R)-1-phenylethyl]morpholin-2-yl}methanone (48a)

and

Phenyl{(2R)-4-[(1R)-1-phenylethyl]morpholin-2-yl}methanone (48b)

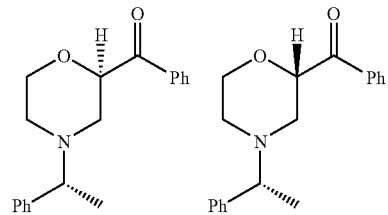

To a stirred solution of 47a,47b (0.57 g, 2.64 mmol) in dry tetrahydrofurane (10 ml) at 0° C. under nitrogen was added a solution of phenylmagnesium chloride in tetrahydrofurane (2.0 M, 2.67 ml) dropwise over 2 minutes. The pale yellow solution was stirred at 0° C. for 30 minutes and then allowed to warm to room temperature. After 2 hours the mixture was cooled, quenched with 2M hydrochloric acid and was stirred vigorously for 1 hour at room temperature. After addition of water and extraction with ethyl acetate, the combined organic layers were washed with brine, dried over magnesium sulphate, filtered and evaporated to give an oil (0.63 g). After purification by column chromatography (eluent: ethyl acetate/hexane gradient 0/100 to 20/80 [v/v]) 48a was obtained as an oil (0.15 g, 19%%); MW 295.38; $C_{19}H_{21}NO_2$; $^1$H NMR (CDCl$_3$) 8.00 (2H, d), 7.60 (1H, t), 7.50 (2H, t), 7.20-7.35 (5H, m), 4.96 (1H, d), 3.93-4.00 (1H, m), 3.70-3.80 (1H, m), 3.41 (1H, q), 3.25 (1H, br, d), 2.59 (1H, br, d), 2.13-2.36 (2H, m), 1.38 (3H, d). m/z [M+H]$^+$ 296 followed by 48b as an oil (0.27 g, 35%%) $^1$H NMR (CDCl$_3$) 7.90 (2H, d), 7.54 (1H, t), 7.45 (2H, t), 7.20-7.38 (5H, m), 4.85 (1H, d), 4.05-4.12 (1H, m), 3.80-3.92 (1H, m), 3.43 (1H, q), 2.86-3.00 (2H, m), 2.29-2.40 (1H, m), 2.21 (1H, t), 1.38 (3H, d). m/z [M+H]$^+$ 296.

(R)-Phenyl{(2S)-4-[(1R)-1-phenylethyl]morpholin-2-yl}methanol (50)

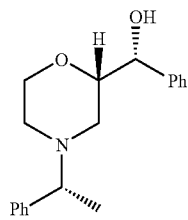

To a stirred solution of 48a (0.08 g, 0.26 mmol) and triphenylsilane (0.34 g, 1.31 mmol) in dichloromethane (4 ml) cooled to 0° C. was added boron trifluoride etherate (0.09 g, 0.66 mmol) followed by trifluoroacetic acid (0.36 ml, 63 mmol). The reaction mixture was allowed to warm to room temperature and diluted after three hours with dichloromethane (20 ml) and neutralised with aqueous sodium bicarbonate. The organic phase was dried over magnesium sulphate, filtered and evaporated to give the required product. This was purified as its hydrochloric acid salt crystallising from isopropanol and diethyl ether (0.05 g, 69%%); MW 297.4; $C_{19}H_{23}NO_2$; $^1$H NMR (CDCl$_3$) on free base 7.08-7.29 (10H, m), 4.78 (1H, d), 3.90-4.00 (1H, m), 3.57-3.68 (2H, m), 3.33 (1H, q), 2.53-2.64 (1H, m), 2.37-2.47 (1H, m), 2.09-2.26 (2H, m), 1.29 (3H, d). m/z [M+H]$^+$ 298.

(R)-Phenyl{(2S)-4-[(1R)-1-phenylethyl]morpholin-2-yl}methyl methanesulphonate (51)

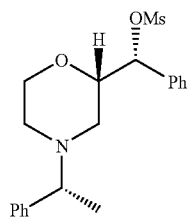

To a solution of 50 (0.05 g, 0.17 mmol) in dichloromethane (1 ml) at room temperature was added polymer supported Hünig's base ((Argonaut, 3.56 mmol/g, 0.089 g, 0.32 mmol, 1.9 eq) and methanesulphonyl chloride (0.02 g, 0.19 mmol). The mixture was stirred under nitrogen for 6 hours then filtered and concentrated in vacuo. The crude product was purified by flash column chromatography (eluent: ethyl acetate/heptane 33/67 (v/v)) to give 51 as a colourless oil (0.035 g, 55%%); MW 375.49; $C_{20}H_{25}NO_4S$ $^1$H NMR (CDCl$_3$) 7.20-7.35 (10H, m), 5.46 (1H, d), 3.79-3.88 (2H, m), 3.59 (1H,td), 3.4 (1H, q), 2.68-2.78 (2H, m), 2.68 (3H, s), 2.03-2.24 (2H, m), 1.34 (3H, d). m/z [M+H]$^+$ 376.

(2S)-4-[(1R)-1-Phenylethyl]-2-((S)-phenyl{[2-(trifluoromethyl)phenyl]thio}methyl)morpholine (52)

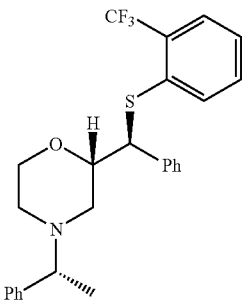

A mixture of 51 (0.035 g, 0.093 mmol), potassium carbonate (0.026 g, 0.19 mmol) and 2-trifluoromethylbenzenethiol (0.084 g, 0.47 mmol) in dry, degassed dimethylformamide (0.5 ml) was stirred under nitrogen at room temperature for 3 days. The reaction mixture was diluted with water and extracted with diethyl ether. The extracts was washed with water and brine, dried over magnesium sulphate, filtered and evaporated to give a colourless oil (0.03 g, 71%). Purification by flash column chromatography (eluent: ethyl acetate/heptane 20/80 [v/v]) gave 52 as a colourless oil (0.03 g, 71%); MW 457.56; $C_{26}H_{26}F_3NOS$ $^1$H NMR (CDCl$_3$) 7.53 (1H, d), 7.10-7.28 (13H, m), 4.39 (1H, d), 3.85-4.04 (2H, m), 3.8 (1H, td), 3.35 (1H, q), 2.70 (1H, d), 2.40 (1H, d), 2.30 (1H, td), 2.10-2.20 (1H, m), 1.29 (3H, d). m/z [M+H]$^+$ 458.

Example 1

(2S)-2-((S)-Phenyl{[2-(trifluoromethyl)phenyl]thio}methyl)moepholine (9)

(S)-Phenyl[(2S)-4-(phenylmethyl)morpholin-2-yl]methyl 2-trifluoromethyl)phenyl sulfide (8)

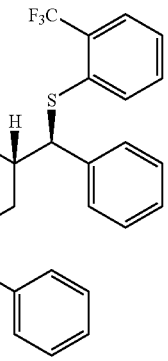

Compound 8 was obtained from 5a (4.00 g, 11.55 mmol), 2-trifluoromethyl thiophenol (2.47 g, 13.86 mmol, 1.2 eq) and caesium carbonate (4.95 g, 15.24 mmol, 1.1 eq) in dimethylformamide (60 ml) as a brown oil following a modification of General Procedure 1 in which the reaction was carried out over 1 hour (6.04 g). The oil was purified by flash column chromatography (eluent: hexane/ethyl acetate gradient 100 to 90/10 [v/v]) to give a yellow oil (4.83 g, 94%); MW 443.54; $C_{25}H_{24}F_3NOS$; $^1$H NMR (CDCl$_3$): 7.60 (1H, dd, 7 Hz, 1 Hz), 7.17-7.39 (13H, m), 4.50 (1H, d, 7 Hz), 3.97-4.12 (2H, m), 3.73 (1H, dt, 10 Hz, 2 Hz), 3.59 (1H, d, 13 Hz), 3.37 (1H, d, 13 Hz), 2.57-2.68 (2H, m); 2.18-2.38 (2H, m); LCMS (2.5 minute method): m/z 445 [M+H]+ @ Rt 1.50 min.

(2S)-2-((S)-Phenyl{[2-(trifluoromethyl)phenyl]thio}methyl)morpholine (9)

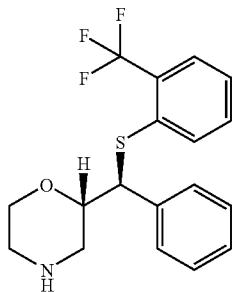

Compound 9 (Example 1) was obtained from 8 (5.25 g, 11.84 mmol), solid supported Hünig's base (Argonaut, 3.56 mmol/g, 6.64 g, 23.67 mmol, 2 eq) and α-chloroethyl chloroformate (3.83 ml, 35.51 mmol, 3 eq) in anhydrous dichloromethane (75 ml) following General Procedure 2a. After evaporation of solvents a light brown solid (5.60 g) was obtained which was recrystailised from iso-propanol. The solid was suspended in ethyl acetate and washed with an aqueous solution of sodium hydroxide (50 ml of a 1M solution). The organic layer was washed with brine, dried over magnesium sulphate and concentrated in vacuo to yield the free amine as a colourless oil (3.10 g, 74%); MW 353.41; $C_{18}H_{18}F_3NOS$;

$^1$H NMR (CDCl$_3$): 7.46 (1H, d, 8 Hz), 7.24 (1H, d, 7 Hz), 7.05-7.2 (7H, m), 4.28 (1H, d, 8 Hz), 3.92 (1H, d, 11 Hz), 3.80 (1H, q, 7 Hz), 3.58 (1H, dt, 2 Hz and 11 Hz), 2.69-2.87 (2H, m), 2.59 (2H, d, 6 Hz), 2.13-1.90 (1H, br s); LCMS (10 minute method): m/z 354 [M+H]+ @ Rt 5.26 min. The hydrochloride salt of 9 was obtained following General Procedure 3.

An alternative method for the preparation of compound 9 (Example 1), according to Scheme 6, is as follows:

To a suspension of polymer supported Hünig's base (0.11 g, 0.40 mmol) and 52 (0.03 g, 0.066 mmol) in dry dichloromethane (1 ml) was added α-chloroethyl chloroformate (0.09 g, 0.066 mmol) at room temperature under nitrogen. The mixture was stirred at room temperature over the weekend then filtered and concentrated in vacuo. This was taken up in methanol, heated at 70° C. for 2 hours, cooled, and purified by SCX chromatography (eluent: ammonia/methanol 1/1 [v/v]) to give 9 as a colourless oil (0.01 g, 43%). The spectroscopic data for 9 obtained by the route outlined here was identical to the data for 9 obtained as described above.

Example 2

(2S)-2-((S)-Phenyl{[2-(thiomethyl)phenyl]thio}methyl)morpholine (11)

(2S)-2-[(S)-{[2-(methylthio)phenyl]thio}(phenyl)methyl]-4-(phenylmethyl)morpholine (10)

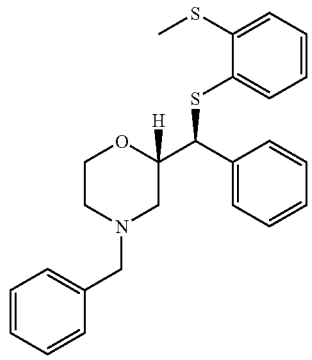

Compound 10 was obtained from 5a (4.0 g, 11.55 mmol), 2-methylsulphenyl-thiophenol (2.17 g, 13.86 mmol, 1.2 eq) and caesium carbonate (4.42 g, 13.63 mmol, 1.18 eq) in dimethylformamide (35 ml) following a modification of General Procedure 1 in which the mixture was heated at 50° C. for 1.5 hours, allowed to cool to room temperature, taken up in methanol and treated with SCX-2 (100 g). The SCX-2 was washed with methanol. 10 was obtained as a white solid (4.92 g) after SCX chromatography (eluent: ammonia/methanol 1/1 [v/v]) and removal of solvents in vacuo. Purification by flash column chromatography (eluent: ethyl acetate/isohexane gradient 10/90 to 30/70 [v/v]) gave 10 as a white solid (4.04 g, 83%); MW 421.63; $C_{27}H_{27}NOS_2$; $^1$H NMR (CDCl$_3$): 7.03-7.15 (6H, m), 6.93-6.99 (2H, m), 6.74 (1H, td, 7 Hz, 1 Hz), 4.31 (1H, d, 8 Hz), 3.95 (1H, br, d, 12 Hz), 3.83 (1H, td, 8 Hz, 3.8 Hz), 3.59 (1H, td, 11 Hz and 3 Hz), 2.82 (1H, td, 12 Hz and Hz), 2.61-2.75 (3H, m), 2.35 (3H, s), 1.73 (1H, br, s); LCMS (6 minute method): m/z 422 [M+H]+ @ Rt 3.36 min.

(2S)-2-((S)-Phenyl{[2-(methylthio)phenyl]thoi}methyl)morpholine (11)

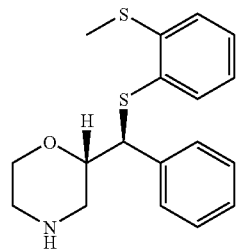

Compound 11 (Example 2) was obtained from 10 (4.02 g, 9.53 mmol), solid supported Hünig's base (Argonaut, 3.56 mmol/g, 5.02 g, 17.87 mmol, 2 eq) and α-chloroethyl chloroformate (3.09 ml, 28.6 mmol, 3 eq) in anhydrous dichloromethane (75 ml) following General Procedure 2a. The mixture was heated at 40° C. for 1.5 hours then left to stir at room temperature overnight. The reaction mixture was filtered and concentrated in vacuo to give a pale orange liquid. This was taken up in methanol (70 ml) and heated at 40° C. for 2 hours. A white solid crashed out of the solution which was taken up in methanol and purified by SCX chromatography (eluent: ammonia/methanol 1/1 [v/v]). After evaporation in vacuo 11 was obtained as a pale yellow oil (3.13 g, 99%); MW 331.50; C₁₈H₂₁NOS₂; ¹H NMR (CDCl₃): 7.03-7.15 (6H, m), 6.93-6.99 (2H, m), 6.74 (1H, td, 7 Hz, 2 Hz), 4.31 (1H, d, 8 Hz), 3.95 (1H, br, d, 12 Hz), 3.83 (1H, td, 8 Hz, 4 Hz), 3.59 (1H, td, 11 Hz, 3 Hz), 2.82 (1H, td, 12 Hz, 3 Hz), 2.61-2.75 (3H, m), 2.35 (3H, s), 1.73 (1H, br, s). Compound 11 was converted into its hydrochloride salt following a modification of General Procedure 3 in which the pale yellow oil was taken up in isopropanol (~200 ml) and filtered. Addition of hydrogen chloride (19 ml of a 1M solution in diethyl ether, 19 mmol) gave a white precipitate to which further diethyl ether (~50 ml) was added. The solid was isolated by filtration and washed with diethyl ether to give the hydrochloride salt of 11 as a white solid (3.03 g, 78%); MW 367.96; C₁₈H₂₂ClNOS₂; ¹H NMR (CDCl₃): 9.94 (2H, br, s), 7.06-7.18 (6H, m), 6.94-7.03 (2H, m), 6.78 (1H, t, 7 Hz), 4.24-4.32 (1H, m), 4.20 (1H, d, 6 Hz), 3.89-4.06 (2H, m), 3.18 (2H, br, t, 12 Hz), 2.99 (2H, br, s), 2.37 (3H, s); LCMS (10 minute method): m/z 332 [M−HCl]+ @ Rt 5.07 min.

Example 3

(2S)-2-[(S)-{[2-(1-methylethyl)phenyl]thio}(phenyl)methylmorpholine (13)

(2S)-2-[(S)-{[2-(1-methylethyl)phenyl]thio}(phenyl)methyl]-4-(phenylmethyl)morpholine (12)

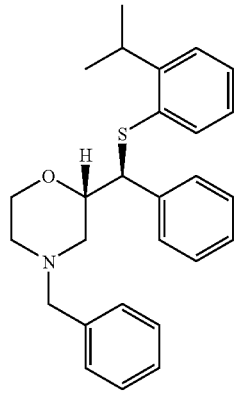

Compound 12 was obtained from 5a (4.04 g, 11.66 mmol), 2-isopropylsulphenyl-thiophenol (2.35 ml, 14 mmol, 1.2 eq) and caesium carbonate (4.56 g, 14 mmol, 1.2 eq) in dimethylformamide (35 ml) following a modification of General Procedure 1 in which the mixture was heated at 90° C. for 20 minutes, allowed to cool to room temperature, taken up in ethyl acetate (50 ml), washed with water and brine, dried over sodium sulphate, filtered and reduced in vacuo to give a yellow oil which was purified by SCX chromatography (eluent: ammonia/methanol 1/1 [v/v]). Removal of solvents in vacuo gave 12 as a white solid (4.45, 91%); MW 417.62; C₂₇H₃₁NOS; ¹H NMR (CDCl₃): 7.14-7.26 (7H, m), 7.03-7.1 (6H, m), 6.86-6.92 (1H, m), 4.10 (1H, d, 8 Hz), 3.88-3.94 (2H, m), 3.62 (1H, td, 11 Hz, 2 Hz), 3.37-3.47 (2H, m), 3.22 (1H, d, 13 Hz), 2.50 (2H, d, 11 Hz), 2.12-2.29 (2H, m), 1.05 (3H, d, 7 Hz), 0.92 (3H, d, 7 Hz); LCMS (6 minute method): m/z 418 [M+H]+ @ Rt 3.72 min.

(2S)-2-[(S)-{[2-(1-methylethyl)phenyl]thio}(phenyl)methyl]morpholine (13)

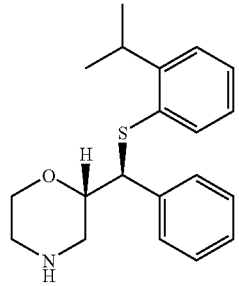

Compound 13 (Example 3) was obtained from 12 (4.44 g, 10.65 mmol), solid supported Hünig's base (Argonaut, 3.56 mmol/g, 6.05 g, 21.54 mmol, 2 eq) and α-chloroethyl chloroformate (3.30 ml, 32.0 mmol, 3 eq) in anhydrous dichloromethane (50 ml) following General Procedure 2a. The mixture was heated at 40° C. for 1.5 hours then left to stir at room temperature overnight. The reaction mixture was filtered and concentrated in vacuo to give a pale yellow liquid. This was taken up in methanol (50 ml) and heated at 60° C. for 1.5 hours. The reaction mixture was allowed to cool to room temperature and purified by SCX chromatography (eluent: ammonia/methanol 1/1 [v/v]) to give 13 as a pale yellow oil; MW 327.49; C₂₀H₂₅NOS; ¹H NMR (CDCl₃): 7.22 (1H, d, 8 Hz), 7.03-7.13 (7H, m), 6.87-6.92 (1H, m), 4.04 (1H, d, 8 Hz), 3.94-3.99 (1H, m), 3.79 (1H, td, 9 Hz, 3 Hz), 3.61 (1H, td, 11 Hz, 3 Hz), 3.41 (1H, sept., 7 Hz), 2.82 (1H, td, 12 Hz and 3 Hz), 2.72 (1H, br, d, 12 Hz), 2.52-2.63 (2H, m), 1.70 (1H, br, s), 1.05 (3H, d, 7 Hz), 0.91 (3H, d, 7 Hz). Compound 13 was converted into its hydrochloride salt following a modification of General Procedure 3 in which the pale yellow oil was taken up in ether (50 ml), and filtered. Addition of hydrogen chloride in dry diethyl ether (19 ml of a 1M solution in diethyl ether) gave a white precipitate to which further diethyl ether (50 ml) was added. The reaction mixture was concentrated and the residue washed with diethyl ether to give a white solid (2.76 g, 69% overall yield from 5a); MW 363.95; C₂₀H₂₅NOS.HCl; ¹H NMR (CDCl₃): 9.91 (2H, br, s), 7.05-7.22 (7H, m), 6.91-6.96 (2H, m), 4.23-4.31 (1H, m), 4.08-3.90 (3H, m), 3.31-3.41 (1H, m), 3.04-3.21 (2H, br, m), 2.91-2.99 (2H, br, m), 1.06 (3H, d, 7 Hz), 0.93 (3H, d, 7 Hz); LCMS (10 minute method): m/z 327 [M−HCl]+ @ Rt 5.7 min.

Example 4

(2S)-2-[(S)-([1,1'-Biphenyl]-2-ylthio)(phenyl)methyl]morpholine (15)

(2S)-2-[(S)-([1,1'-Biphenyl]-2-ylthio)(phenyl)methyl]-4-(phenylmethyl)morpholine (14)

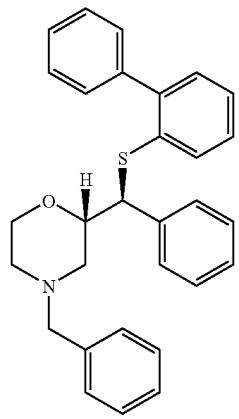

Compound 14 was obtained from 5a (2.16 g, 6.24 mmol), 2-phenylsulphenyl-thiophenol (2.35 ml, 14 mmol, 1.2 eq) and caesium carbonate (2.43 g, 7.5 mmol, 1.2 eq) in dimethylformamide (50 ml) following a modification of General Procedure 1 in which the mixture was heated at 90° C. for 20 minutes, allowed to cool to room temperature, taken up in ethyl acetate (50 ml), washed with water and brine, dried over sodium sulphate, filtered and reduced in vacuo to give a yellow oil. Purification by SCX-chromatography (eluent: ammonia/methanol 1/1 [v/v]) followed by evaporation in vacuo gave 14 as a white solid (0.59 g, 90%); MW 451.64; $C_{30}H_{29}NOS$; $^1H$ NMR ($CDCl_3$): 6.93-7.34 (19H, m), 3.92 (1H, br, d, 6 Hz), 3.63-3.76 (2H, m), 3.45 (1H, t, 10 Hz), 3.33 (1H, d, 13 Hz), 3.17 (1H, d, 12 Hz), 2.39 (1H, d, 12 Hz), 2.20 (1H, d, 11 Hz), 1.97-2.07 (1H, m), 1.82-1.92 (1H, m); LCMS (6 minute method): m/z 452 [M+H]+ @ Rt 3.69 min.

(2S)-2-[(S)-([1,1'-Biphenyl]-2-ylthio)(phenyl)methyl]morpholine (15)

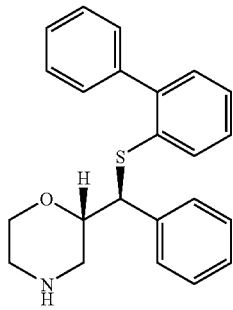

Compound 15 (Example 4) was obtained from 14 (2.95 g, 6.54 mmol), solid supported Hünig's base (Argonaut, 3.56 mmol/g, 13.06 g, 21.54 mmol, 2 eq) and α-chloroethyl chloroformate (2.0 ml, 19.6 mmol, 3 eq) in anhydrous dichloromethane (50 ml) following General Procedure 2a. The reaction mixture was concentrated in vacuo to give a pale yellow liquid. This was taken up in methanol (70 ml) and heated at 40° C. for 2 hours. A white solid crashed out of the solution which was taken up in methanol and purified by SCX-chromatography (eluent: ammonia/methanol 1/1 [v/v]). After removal of solvents in vacuo 15 was obtained as a pale yellow oil; MW 361.51; $C_{23}H_{23}NOS$; $^1H$ NMR ($CDCl_3$): 7.0-7.45 (14H, m), 3.95 (1H, d, 8 Hz), 3.65-3.85 (2H, m), 3.35 (1H, d, 12 Hz), 3.2 (1H, d, 12 Hz), 2.45 (1H, d, 10 Hz), 2.20 (1H, d, 10 Hz), 2.0-2.15 (1H, m), 1.8-2.0 (1H, m); LCMS (12 minute method): m/z 363 [M+H]+ @ Rt 3.00 min. 15 was converted into its hydrochloride salt following a modification of General Procedure 3 in which the pale yellow oil was taken up in isopropanol (~200 ml), and filtered. Addition of hydrogen chloride (19 ml of a 1M solution in diethyl ether) gave a white precipitate to which further diethyl ether (~50 ml) was added. The solid was isolated by filtration and washed with diethyl ether to give the hydrochloride salt of 15 as a white solid (1.95 g, 75% overall yield from 5a); MW 397.97; $C_{23}H_{23}NOS.HCl$; $^1H$ NMR ($CDCl_3$): 9.80 (2H, br, s), 7.38-7.03 (12H, m), 6.90-6.96 (2H, m), 3.85-4.00 (2H, m), 3.72-3.82 (1H, m), 3.66 (1H, d, 5 Hz), 2.98-3.10 (1H, m), 2.81 (1H, br, s), 2.62 (2H, br, s); LCMS (12 minute method): m/z 362 [M+H]+ @ Rt 2.99 min.

Example 5

(2S)-2-[(S)-[(2-Fluorophenyl)thio](phenyl)methyl]morpholine (17)

(2S)-2-[(S)-[(2-Fluorophenyl)thio](phenyl)methyl]4-phenylmethyl)morpholine (16a)

and (2R)-2-[(R)-[(2-Fluorophenyl)thio](phenyl)methyl]-4-phenylmethyl)morpholine (16b)

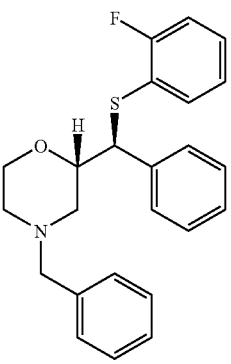

Compounds 16a,16b were obtained from 5a,5b (0.114 g, 0.33 mmol), 2-fluorothiophenol (0.045 g, 0.36 mmol, 1.2 eq) and caesium carbonate (0.12 g, 0.36 mmol, 1.2 eq) in dimethylformamide (50 ml) following General Procedure 1 as a pale yellow oil (0.14 g, 65%); MW 393.53; $C_{24}H_{24}FNOS$; $^1H$ NMR ($CDCl_3$): 7.12-7.36 (12H, m), 6.87-6.99 (2H, m), 4.48 (1H, d, 8 Hz), 4.00-4.11 (2H, m), 3.77 (1H, td, 11 Hz, 2 Hz), 3.60 (1H, d, 13 Hz), 3.37 (1H, d, 13 Hz); 2.63 (2H, t, 10 Hz), 2.16-2.31 (2H, m); LCMS (2.5 minute method): m/z 394 [M+H]+ @ $R_t$ 1.41 min.

(2S)-2-[(S)-[(2-Fluorophenyl)thio](phenyl)methyl]morpholine (17)

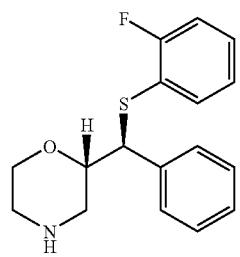

Compound 17 (Example 5) was obtained from 16a,16b (0.72 g, 0.18 mmol), solid supported Hünig's base (Argonaut, 3.56 mmol/g, 2.0 g, 0.56 mmol, 3 eq) and α-chloroethyl chloroformate (0.62 ml, 0.56 mmol, 3 eq) in anhydrous dichloromethane (5 ml) following General Procedure 2a as a viscous yellow oil (0.046 g, 82%) from which 17 was obtained as a single isomer after separation by chiral HPLC (0.016 g); Chiral LC (AD): 10.83 min. LC purity=91% (UV254 nm)/98% (ELS); LCMS (10 minute method): m/z 304 [M+H]+ @ Rt 5.82 min; HPLC purity=84% (UV215 nm)/98% (ELS); MW 303.41; $C_{17}H_{18}FNOS$; $^1H$ NMR ($CDCl_3$): 7.13-7.00 (7H, m), 6.87-6.76 (2H, m), 4.29 (1H, d, 9 Hz), 3.98-3.93, (1H, m), 3.78 (1H, td, 9 Hz and 4 Hz), 3.60 (1H, td, 11 Hz and 3 Hz), 2.82 (1H, td, 12 Hz, 3 Hz), 2.76-2.70 (1H, m), 2.57-2.53, (2H, m), NH signal not observed; LCMS (10 minute method): m/z 304 [M+H]+ @ Rt 5.84 min; HPLC purity=100%% (BLS). Compound 17 was converted into its hydrochloride salt following General Procedure 3.

Example 6

(2S)-2-[(S)-[(2-Ethylphenyl)thio](phenyl)methyl]morpholine (19)

(2S)-2-[(S)-[(2-Ethylphenyl)thio](phenyl)methyl]-4-(phenylmethyl)morpholine (18a)

and (2R)-2-[(R)-[(2-Ethylphenyl)thio](phenyl)methyl]-4-(phenylmethyl)morpholine (18b)

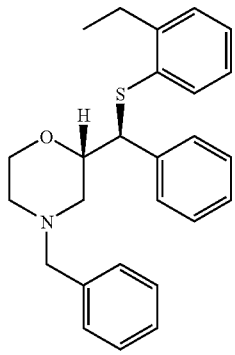

Compounds 18a,18b were obtained from 5a,5b (0.2 g, 0.58 mmol), 2-ethyl-thiophenol (0.16 g, 1.16 mmol, 2 eq) and caesium carbonate (0.23 g, 0.7 mmol, 1.2 eq) in dimethylformamide (5 ml) following modification of General Procedure 1 in which the reaction mixture was heated to 95° C. for 2 hours. After purification by flash column chromatography (eluent: ethyl acetate/hexane 9/1 [v/v]) 18a,18b was obtained as a white solid (0.15 g, 65%%); MW 403.59; $C_{26}H_{29}NOS$; $^1H$ NMR ($CDCl_3$): 6.96-7.40 (14H, m), 4.22 (1H, d, 7 Hz), 3.96-4.01 (2H, m), 3.72 (1H, td, 11 Hz and 2 Hz), 3.52 (1H, d, 13 Hz), 3.32 (1H, d, 13 Hz), 2.68 (2H, q, 8 Hz), 2.59 (2H, br d, 12 Hz), 2.06-2.21 (2H, m), 1.12 (3H, t, 7 Hz); LCMS (2.5 minute method) m/z 404 [M+H]+ @ Rt 1.49 min.

(2S)-2-[(S)-[(2-Ethylphenyl)thio](phenyl)methyl]morpholine (19)

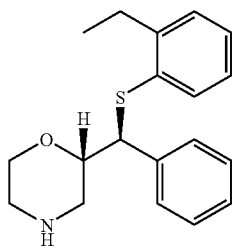

Compound 19 (Example 6) was obtained from 18a,18b (0.18 g, 0.52 mmol), solid supported Hünig's base (Argonaut, 3.56 mmol/g, 3.7 g, 1.04 mmol, 2 eq) and α-chloroethyl chloroformate (0.34 ml, 3.12 mmol, 3 eq) in anhydrous dichloromethane (5 ml) following General Procedure 2a as a viscous yellow oil (0.21 g, 86%) from which 19 was obtained after separation by chiral HPLC on chiral OD semi-preparative column; chiral LC (OD): 15.95 min. LC purity=100% (UV254 nm)/100% (LS); MW 313.47; $C_{19}H_{23}NOS$; $^1H$ NMR ($CDCl_3$): 7.17 (1H, d, 8 Hz), 7.12-7.05 (5H, m), 7.01 (2H, d, 4 Hz), 6.87-6.93 (1H, m), 4.07 (1H, d, 8 Hz), 3.92-3.97 (1H, m), 3.74-3.80 (1H, m), 3.59 (1H, td, 11 Hz, 3 Hz), 2.80 (1H, td, 12 Hz and 3 Hz), 2.71 (1H, br, d, 12 Hz), 2.63-2.54 (4H, m), 1.64 (1H, br, s), 1.04 (3H, t, 8 Hz); LCMS (10 minute method): m/z 314 [M+H]+ @ Rt 5.92 min. 19 was converted into its hydrochloride salt following General Procedure 3; MW 349.93; $C_{19}H_{23}NOS.HCl$; $^1H$ NMR ($CDCl_3$): 10.10 (2H, br, s), 7.13-7.28 (8H, m), 7.02-7.08 (1H, m), 4.36 (1H, br, s), 4.01-4.17 (3H, br, m), 3.16-3.31 (2H, br, m), 2.92-3.09 (2H, br, m), 2.71 (2H, q, 8 Hz), 1.15 (3H, t, 7 Hz).

Example 7

(2S)-2-[(S)-{[2-(Methyloxy)phenyl]thio}(phenyl)methyl]morpholine (21)

(2S)-2-[(S)-{[2-(Methyloxy)phenyl]thio}(phenyl)methyl]-4-(phenylmethyl)morpholine (20a)

and (2R)-2-[(R)-{[2-(Methyloxy)phenyl]thio}(phenyl)methyl]-4-(phenylmethyl)morpholine (20b)

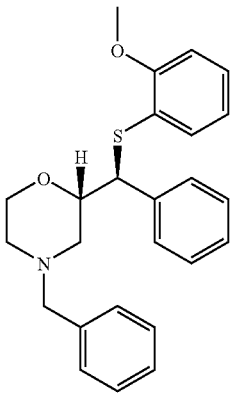

Compounds 20a,20b were obtained from 5a,5b (0.18 g, 0.52 mmol), 2-methoxy thiophenol (0.074 ml, 0.57 mmol, 1.2 eq) and caesium carbonate (0.17 g, 0.52 mmol, 1.2 eq) in dimethylformamide (5 ml) following modification of General Procedure 1 in which the reaction was heated at 95° C. for 2.5 hours. After purification by flash column chromatography (eluent: ethyl acetate/hexane gradient 15/85 to 25/75 [v/v]) 20a,20b was obtained as a viscous yellow oil (0.17 g, 83%); MW 405.56; $C_{25}H_{27}NO_2S$; $^1H$ NMR ($CDCl_3$): 7.01-7.26 (12H, m), 6.58-6.63 (2H, m), 4.39 (1H, d, 7 Hz), 3.86-3.91 (2H, m), 3.71 (3H, s), 3.56-3.62 (1H, m), 3.42 (1H, d, 11 Hz); 3.21 (1H, d, 11 Hz), 2.46-2.52 (2H, m), 2.01-2.11 (2H, m); LCMS (10 minute method): m/z 406 [M+H]$^+$ @ $R_T$ 6.09 min.

(2S)-2-[(S)-{[2-(Methyloxy)phenyl]thio}(phenyl)methyl]morpholine (21)

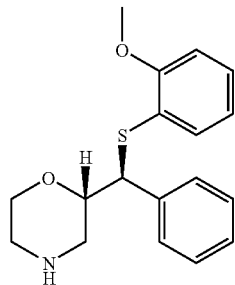

Compound 21 (Example 7) was obtained from 20a,20b (0.1 g, 0.25 mmol), solid supported Hünig's base (Argonaut, 3.56 mmol/g, 1.78 g, 0.5 mmol, 2 eq) and α-chloroethyl chloroformate (0.16 ml, 1.5 mmol, 3 eq) in anhydrous dichloromethane (5 ml) following General Procedure 2a as a viscous yellow oil (0.06 g, 77%) from which 21 was obtained after separation by chiral HPLC on a Chiralcel OJ semi-preparative column. Chiral LC: 11.45 min. LC purity=100%; MW 315.44; $C_{18}H_{21}NO_2S$; $^1H$ NMR ($CDCl_3$): 7.14-7.34 (7H, m), 6.74-6.84 (2H, m), 4.50 (1H, d, 8 Hz), 4.10 (1H, d, 11 Hz), 3.85-4.00 (4H, m), 3.74 (1H, dt, 1 Hz, 11 Hz), 2.82-3.02 (2H, m), 2.66-3.02 (3H, m); LCMS (10 minute method): m/z 316 $[M+H]^+$ @ $R_t$ 4.87 min. 21 was converted its hydrochloride salt following General Procedure 3.

Example 8

(2S)-2-[(S)-({2-[(1-Methylethyl)oxy]phenyl}thio)(phenyl)methyl]morpholine (23)

(2S)-2-[(S)-({2-[(1-Methylethyl)oxy]phenyl}thio)(phenyl)methyl]-4-(phenylmethyl)morpholine (22a)

and (2R)-2-[(R)-({2-[(1-Methylethyl)oxy]phenyl}thio)(phenyl)methyl]-4-(phenylmethyl)morpholine (22b)

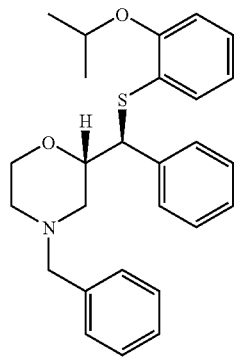

Compounds 22a,22b were obtained from 5a,5b (0.57 g, 1.7 mmol), 2-isopropoxy-thiophenol (0.94 g, 5.61 mmol) and caesium carbonate (2.18 g, 6.72 mmol, 1.2 eq) in dimethylformamide (15 ml) following modification of General Procedure 1 in which the reaction mixture was heated to 95° C. for 3 hours. After purification by SCX chromatography (eluent: ammonia/methanol 1/1 [v/v]) 22a,22b was obtained as a dark yellow oil (0.56 g, 76%%); MW 433.62; $C_{27}H_{31}NO_2S$; $^1H$ NMR ($CDCl_3$): 7.01-7.24 (7H, m), 6.94-7.09 (5H, m), 6.64 (1H, d, 8 Hz), 6.56 (1H, td, 8 Hz, 1 Hz), 4.42-4.51 (2H, m), 3.83-3.92 (2H, m), 3.56 (1H, td, 11 Hz and 3 Hz), 3.42 (1H, d, 13 Hz), 3.24 (1H, d, 13 Hz), 2.52 (1H, d, 11 Hz), 2.46 (1H, d, 11 Hz), 2.05-2.17 (2H, m), 1.29 (3H, d, 6 Hz), 1.27 (3H, d, 6 Hz); LCMS (2.5 minute method): m/z 434 $[M+H]^+$ @ $R_T$ 1.44 min.

(2S)-2-[(S)-({2-[(1-Methylethyl)oxy]phenyl}thio)(phenyl)methyl]morpholine (23)

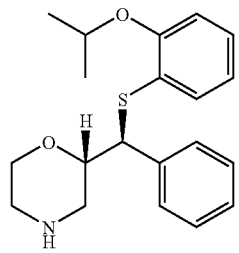

Compound 23 (Example 8) was obtained from 22a,22b (0.56 g, 1.3 mmol), solid supported Hünig's base (Argonaut, 3.56 mmol/g, 0.73 g, 2.6 mmol, 2 eq) and α-chloroethyl chloroformate (0.16 ml, 1.5 mmol, 3 eq) in anhydrous dichloromethane (5 ml) following General Procedure 2a as a viscous yellow oil (0.41 g, 93%) after separation using chiral HPLC on a OD semi-preparative column. Chiral LC (OD): 12.51 min. LC purity=100% (UV254 nm)/100% (ELS); MW 343.49; $C_{20}H_{25}NO_2S$; $^1H$ NMR ($CDCl_3$): 7.13-7.20 (1H, m), 6.96-7.12 (6H, m), 6.67 (1H, d, 8 Hz), 6.59 (1H, td, 7 Hz, 1 Hz), 4.48 (1H, sept., 6 Hz), 4.38 (1H, d, 7 Hz), 3.90-3.95 (1H, m), 3.73 (1H, td, 8 Hz, 4 Hz), 3.54 (1H, td, 11 Hz and 3 Hz), 2.79 (1H, td, 12 Hz and 3 Hz), 2.62-2.72 (3H, m), 1.55 (1H, br, s), 1.32 (3H, d, 6 Hz), 1.29 (3H, d, 6 Hz); LCMS (10 minute method): m/z 344 [M+H]+ @ Rt 6.19 min; HPLC purity=92% (UV215 nm). 23 was converted into its hydrochloride salt following General Procedure 3; MW 379.95; $C_{20}H_{25}NO_2S.HCl$; $^1H$ NMR ($CDCl_3$): 9.81-10.04 (2H, br, m), 7.03-7.25 (7H, m), 6.71 (1H, d, 8 Hz), 6.63 (1H, t, 7 Hz), 4.51 (1H, sept., 6 Hz), 4.31 (1H, d, 6 Hz), 4.15-4.23 (1H, m), 3.83-4.03 (2H, m), 3.05-3.18 (2H, m), 2.80-3.03 (2H, m), 1.31 (3H, d, 6 Hz), 1.29 (3H, d, 6 Hz).

Example 9

2-{[(S)-(2S)-Morpholin-2-yl(phenyl)methyl]thio}phenyl trifluoromethyl ether (25)

(2S)-4-(Phenylmethyl)-2-[(S)-phenyl({2-[(trifluoromethyl)oxy]phenyl}thio)methyl]morpholine (24a)

and (2S)-4-(Phenylmethyl)-2-[(S)-phenyl({2-[(trifluoromethyl)oxy]phenyl}thio)methyl]morpholine (24b)

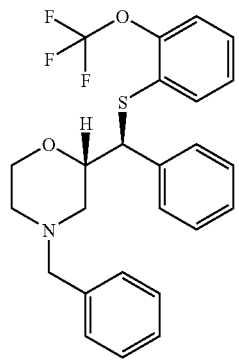

Compounds 24a,24b were obtained from 5a,5b (0.011 g, 0.33 mmol), 2-trifluoromethoxythiophenol (1.2 eq, 0.077 g, 0.39 mmol) and caesium carbonate (0.15 g, 0.47 mmol, 1.2 eq) in dimethylformamide (15 ml) following modification of General Procedure 1 in which the reaction was heated at 95° C. for 1.5 hours. The reaction mixture was allowed to cool to room temperature, diluted with ethyl acetate (20 ml), washed sequentially with water and brine, dried over sodium sulphate and finally concentrated in vacuo to give a pale yellow oil (0.14 g, 92%); MW 459.53; $C_{25}H_{24}F_3NO_2S$; $^1H$ NMR (CDCl$_3$): 7.13-7.41 (13H, m), 7.08-7.13 (1H, m), 4.51 (1H, d, 8 Hz), 3.99-4.07 (2H, m), 3.73 (1H, td, 9 Hz, 2.5 Hz), 3.57 (1H, d, 13 Hz), 3.37 (1H, d, 13 Hz); 2.57-2.66 (2H, m), 2.20-2.31 (2H, m); LCMS (10 minute method): m/z 460 $[M+H]^+$ @ $R_t$ 6.69 min.

2-{[(S)-(2S)-Morpholin-2-yl(phenyl)methyl]thio}phenyl trifluoromethyl ether (25)

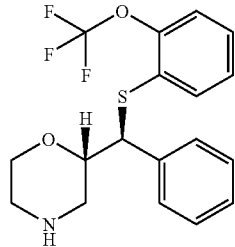

Compound 25 (Example 9) was obtained from 24a,24b (0.06 g, 0.13 mmol), solid supported Hünig's base (Argonaut, 3.56 mmol/g, 0.073 g, 0.026 mmol, 2 eq) and α-chloroethyl chloroformate (0.04 ml, 0.39 mmol, 3 eq) in anhydrous dichloromethane (5 ml) following General Procedure 2a as a viscous yellow oil (0.021 g, 44%) from which 25 was obtained after separation using chiral HPLC on a OD semi-preparative column. Chiral LC (03): 12.60 min. LC purity=98% ($UV_{254\ nm}$)/100% (ELS); MW 369.41; $C_{18}H_{18}F_3NO_2S$; $^1H$ NMR (CDCl$_3$): 7.02-7.21 (8H, m), 6.91-6.96 (1H, m), 4.28 (1H, d, 8 Hz), 3.93 (1H, br, d 11 Hz), 3.75-3.81 (1H, m), 3.60 (1H, td, 11 Hz and 3 Hz), 2.71-2.86 (2H, m), 2.61 (2H, d, 6 Hz), 1.90 (1H br, s); LCMS (10 minute method): m/z 370 $[M+H]^+$ @ $R_t$ 5.86 min.

Example 10

(2S)-2-[(S)-[(2-Methylphenyl)thio](phenyl)methyl]morpholine (27)

(2S)-2-[(S)-[(2-Methylphenyl)thio](phenyl)methyl]-4-(phenylmethyl)morpholine (26a)

and (2R)-2-[(R)-[(2-Methylphenyl)thio](phenyl)methyl]-4-(phenylmethyl)morpholine (26b)

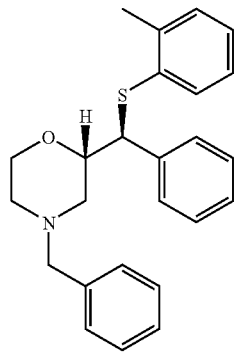

Compounds 26a,26b were obtained from 5a,5b (0.1 g, 0.29 mmol), 2-methyl thiophenol (0.04 ml, 0.31 mmol) and caesium carbonate (0.125 g, 0.37 mmol, 1.2 eq) in dimethylformamide (15 ml) following General Procedure 1 as a colourless oil (0.13 g, 85%); MW 389.56; $C_{25}H_{27}NOS$; $^1H$ NMR (CDCl$_3$): 6.84-7.24 (14H, m), 4.14 (1H, d, 8 Hz), 3.85-3.95 (2H, m), 3.60 (1H, dt, 10 Hz, 3 Hz), 3.42 (1H, d, 13 Hz); 3.21 (1H, d, 13 Hz), 2.46-2.54 (2H, m), 2.18 (3H, s), 1.97-2.13 (2H, m); LCMS (2.5 minute method): m/z 390 $[M+H]^+$ @ $R_T$ 1.49 min.

(2S)-2-[(S)-[(2-Methylphenyl)thio](phenyl)methyl]morpholine (27)

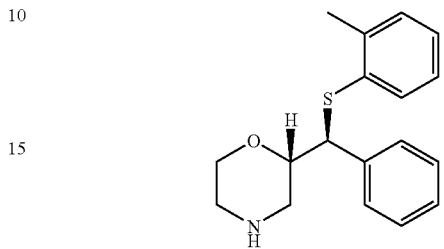

Compound 27 (Example 10) was obtained from 26a,26b (0.04 g, 0.12 mmol), solid supported Hünig's base (Argonaut, 3.56 mmol/g, 0.89 g, 0.24 mmol, 2 eq) and α-chloroethyl chloroformate (0.04 ml, 0.36 mmol, 3 eq) in anhydrous dichloromethane (5 ml) following General Procedure 2a as a viscous yellow oil (0.03 g, 75%) from which 27 was obtained after chiral separation. Chiral LC (OJ): 15.84 min. LC purity=98.57% ($UV_{254\ nm}$); MW 299.44; $C_{18}H_{21}NOS$; $^1H$ NMR (CDCl$_3$): 6.86-7.21 (9H, m), 4.08 (1H, d, 7 Hz), 3.75 (1H, br s), 3.58 (1H, br s), 2.34-3.1 (4H, m), 2.20 (3H, s); 1.41-2.04 (2H, m); LCMS (10 minute method): m/z 300 $[M+H]^+$ @ $R_T$ 5.08 min. 27 was converted into its hydrochloride salt following General Procedure 3.

Example 11

(2S)-2-{(S)-Phenyl[(2-propylphenyl)thio]methyl}morpholine (29)

(S)-Phenyl[(2S)-4-(phenylmethyl)morpholin-2-yl]methyl-2-propylphenyl sulfide (28a) and

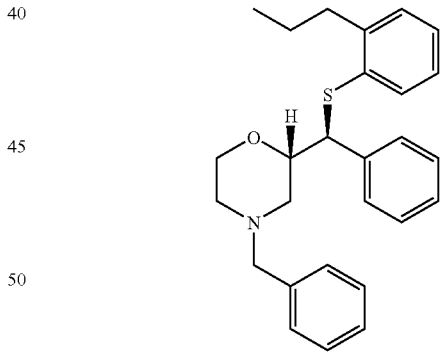

Compounds 28a,28b were obtained from 5a (0.53 g, 1.50 mmol), 2-n-propyl thiophenol (0.025 g, 1.65 mmol) and caesium carbonate (0.59 g, 1.8 mmol, 1.2 eq) in dimethylformamide (5 ml) following a modification of General Procedure 1 in which the reaction was heated at 95° C. for 3 hours. After purification by SCX column chromatography (eluent: ammonia/methanol 1/1 [v/v]) 28a,28b was obtained as a dark yellow oil (0.56 g, 90%%); MW 417.62; $C_{27}H_{31}NOS$; $^1H$ NMR (CDCl$_3$): 7.23-7.12 (6H, m), 7.06-7.11 (5H, m), 6.97-6.99 (2H, m), 6.87-6.92 (1H, m), 4.13 (1H, d, 8 Hz), 3.86-3.94 (2H, m), 3.61 (1H, td, 11 Hz, 2 Hz), 3.44 (1H, d, 13 Hz), 3.23 (1H, d, 13 Hz), 2.46-2.59 (4H, m), 2.01-2.14 (2H, m), 1.34-1.52 (2H, m), 0.83 (3H, t, 7 Hz); LCMS (2.5 minute method): m/z 418 $[M+H]^+$ @ $R_t$ 1.55 min.

39

(2S)-2-{(S)-Phenyl[(2-propylphenyl)thio]methyl}morpholine (29)

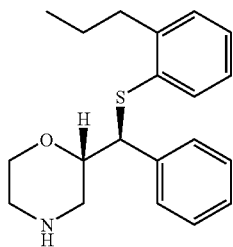

Compound 29 (Example 11) was obtained from 28a,28b (0.56 g, 1.35 mmol), solid supported Hünig's base (Argonaut, 3.56 mmol/g, 0.75 g, 2.7 mmol, 2 eq) and α-chloroethyl chloroformate (0.44 ml, 4.05 mmol, 3 eq) in anhydrous dichloromethane (5 ml) following General Procedure 2a as a viscous yellow oil (0.41 g, 93%); MW 327.49; $C_{20}H_{25}NOS$; $^1H$ NMR ($CDCl_3$): 7.17 (1H, br, d, 7 Hz), 7.07-7.12 (5H, m), 6.96-7.00 (2H, m), 6.88-6.93 (1H, m), 4.07 (1H, d, 8 Hz), 3.93-3.98 (1H, m), 3.74-3.80 (1H, m), 3.60 (1H, td, 11 Hz, 3 Hz), 2.81 (1H, td, 12 Hz and 3 Hz), 2.72 (1H, br, d, 12 Hz), 2.48-2.62 (4H, m), 1.36-1.59 (3H, m), 0.83 (3H, t, 7 Hz); LCMS (2.5 minute method): m/z 328 $[M+H]^+$ @ $R_t$ 1.40 min (single major peak).

Example 12

Methyl 2-{[(S)-(2S)-morpholin-2-yl(phenyl)methyl]thio}benzoate (31)

Methyl-2-({(S)-phenyl[(2S)-4-(phenylmethyl)morpholin-2-yl]methyl}thio)benzoate (30a)

and

Methyl-2-({(R)-phenyl[(2R)-4-(phenylmethyl)morpholin-2-yl]methyl}thio)benzoate (30b)

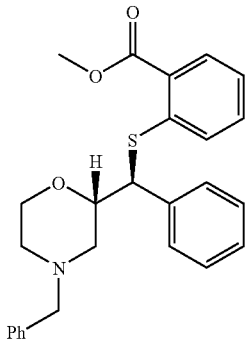

Compounds 30a,30b were obtained from 5a,5b (0.5 g, 1.45 mmol), methyl thiosalicylate (0.49 g, 2.89 mmol) and potassium carbonate (0.21 g, 1.52 mmol) in dry tetrahydrofurane (5 ml) following modification of General Procedure 1 in which the solvents were degassed and purged with nitrogen before the addition of methyl thiosalicylate. The reaction mixture was stirred at room temperature for 18 hours after which time the reaction mixture was poured onto water and extracted twice with diethyl ether. The organic layers were washed with water, dried and evaporated in vacuo. After purification by SCX column chromatography (eluent: ammonia/methanol 1/1 [v/v]) 30a,30b was obtained as a colourless solid (0.18 g, 29%%); MW 433.57; $C_{26}H_{27}NO_3S$; $^1H$ NMR ($CDCl_3$): 8.65-8.85 (1H, m), 6.95-7.45 (13H, m), 4.45 (1H, d, 8 Hz), 3.85-4.05 (1H, m), 3.8 (3H, s), 3.65 (1H, dt, 1 Hz and 7 Hz), 3.55 (1H, d, 11 Hz), 3.25 (1H, d, 11 Hz), 2.5-2.6 (2H, m); 2.0-2.15 (2H, m); FIA: m/z 462 $[M+H]^+$.

40

Methyl 2-{[(S)-(2S)-morpholin-2-yl(phenyl)methyl]thio}benzoate (31)

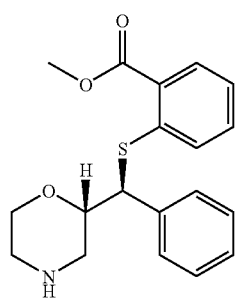

Compound 31 (Example 12) was obtained from 30a,30b (0.2 g, 0.46 mmol), solid supported Hünig's base (Argonaut, 3.56 mmol/g, 0.08 g, 2.77 mmol, 6 eq) and α-chloroethyl chloroformate (0.5 ml, 4.62 mmol, 10 eq) in anhydrous dichloromethane (5 ml) following General Procedure 2a as a white solid (0.16 g, 91%) from which 31 was obtained after separation using chiral HPLC on chiral OJ semi-preparative column. Chiral LC (OJ): 12.32 min. LC purity=100% ($UV_{254\ nm}$); MW 343.45. 31 was converted into its hydrochloride salt following General Procedure 3; $^1H$ NMR ($d_6$-DMSO): 9.30-9.5 (1H, m), 7.75-7.80 (1H, m), 7.1-7.55 (8H, m), 4.82 (1H, d, 8 Hz), 3.95-4.15 (2H, m), 3.65-3.9 (3H, m), 3.55 (3H, s), 2.80-3.25 (2H, m).

Example 13

(2S)-2-((S)-(3-Fluorophenyl){[2-(trifluoromethyl)phenyl]thio}methyl)morpholine (33)

(2S)-2-((S)-(3-Fluorophenyl){[2-(trifluoromethyl)phenyl]thio}methyl)-4-(phenylmethyl)morpholine (32a)

and (2R)-2-((R)-(3-Fluorophenyl){[2-(trifluoromethyl)phenyl]thio}methyl)-4-(phenylmethyl)morpholine (32b)

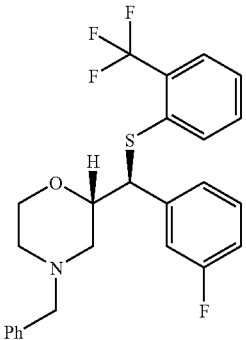

Compounds 32a,32b were obtained as outlined in Scheme 5 from 38a,38b (0.33 g, 0.91 mmol) following General Procedure 4 as a white solid after column chromatography (0.28 g, 67%); MW 461.53; $C_{25}H_{23}F_4NOS$; $^1H$ NMR ($CDCl_3$) 6.75-7.65 (1H, m), 6.85-7.33 (12H, m), 4.45 (2H, d, 8 Hz), 3.6-3.75 (2H, m), 3.45 (1H, d 12 Hz), 3.3 (1H, d 12 Hz), 2.45-2.7 (2H, br, m),), 2.1-2.3 (2H, br, m); FIA: m/z 462 $[M+H]^+$.

(2S)-2-((S)-(3-Fluorophenyl){[2-(trifluoromethyl)phenyl]thio}methyl)morpholine (33)

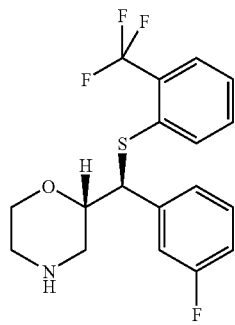

Compound 33 (Example 13) was obtained from 32a,32b (0.28 g, 0.615 mmol), solid supported Hünig's base (Argonaut, 3.56 mmol/g, 0.19 g, 0.68 mmol, 1.1 eq) and α-chloroethyl chloroformate (0.07 ml, 0.68 mmol, 1.1 eq) in anhydrous dichloromethane (5 ml) following General Procedure 2a as a colourless oil (0.22 g, 95%) from which 33 was obtained after chiral chromatography on a Chiralcel OJ semi-preparative column. Chiral LC (OJ): 13.33 min. LC purity=98.37% ($UV_{254\ nm}$); MW 371.4; $C_{18}H_{17}F_4NOS$. LCMS (12 minute method): m/z 372 [M+H]+ @ Rt 5.2 min. 33 was converted into its hydrochloride salt following General Procedure 3; MW 407.86; $C_{18}H_{17}F_4NOS \cdot HCl$; $^1H$ NMR ($CDCl_3$) 9.8-10.2 (1H, br), 7.4-7.6 (1H, m), (6.85-7.45 (8H, m), 4.05-4.45 (4H, br, m), 2.90-3.41 (4H, br, m).

Example 14

(2S)-2-((S)-(4-Chlorophenyl){[2-(trifluoromethyl)phenyl]thio}methyl)morpholine (35)

(2S)-2-((S)-(4-Chlorophenyl){[2-(trifluoromethyl)phenyl]thio}methyl)-4-(phenylmethyl)morpholine (34a)

and (2R)-2-((R)-(4-Chlorophenyl){[2-(trifluoromethyl)phenyl]thio}methyl)-4-(phenylmethyl)morpholine (34b)

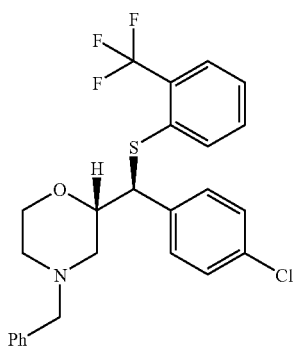

Compounds 34a,34b were obtained as outlined in Scheme 5 from 39a,39b (0.4 g, 1.06 mmol, 1.1 eq), cesium carbonate (0.33 g, 1.0 mmol, 1.1 eq), and 2-trifluoromethyl benzene thiol (0.19 g, 1.06 mmol, 1.1 eq) following a modification of General Procedure 1 in which the reaction was stirred at room temperature for 1.5 hours as a white solid after column chromatography (eluent: gradient hexane/ethyl acetate 10/90 to 25/75[v/v]) (0.409 g, 80%); MW 477.98; $C_{25}H_{23}F_3ClNOS$, $^1H$ NMR ($CDCl_3$) 7.1-7.65 (13H, m), 4.45 (1H, d, 8 Hz), 3.85-4.0 (2H, m), 3.55 (1H, m), 3.3 (1H, d 12 Hz), 3.3 (1H, d 12 Hz), 2.45-2.65 (2H, br,), 2.1-2.3 (2H, br, m); FIA: m/z 478 [M+H]+.

(2S)-2-((S)-(4-Chlorophenyl){[2-(trifluoromethyl)phenyl]thio}methyl)morpholine (35)

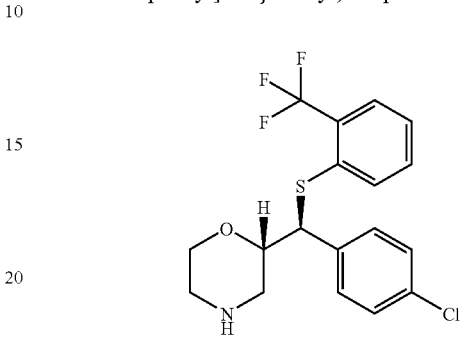

Compound 35 (Example 14) was obtained from 34a,34b (0.41 g, 0.86 mmol), solid supported Hünig's base (Argonaut, 3.56 mmol/g, 0.27 g, 0.94 mmol, 1.1 eq) and α-chloroethyl chloroformate (0.10 ml, 0.94 mmol, 1.1 eq) in anhydrous dichloromethane (5 ml) following General Procedure 2a as a colourless oil (0.28 g, 84% yield) from which 35 was obtained after separation using chiral HPLC on a ChiralPak-AD OJ semi-preparative column; MW 387.85; $C_{18}H_{17}ClF_3NOS$; LCMS (12 minute method): m/z 372 [M+H]+ @ Rt 5.2 min. 35 was converted into its hydrochloride salt following General Procedure 3; MW 423.96; $C_{18}H_{17}ClF_3NOS \cdot HCl$; $^1H$ NMR ($CDCl_3$): 9.8-10.2 (1H, br), 7.4-7.6 (1H, m), 7.07-7.35 (7H, m), 3.8-4.45 (4H, br, m), 2.85-3.45 (4H, br, m).

Example 15

(2S)-2-((S)-(2-Fluorophenyl){[2-(methyloxy)phenyl]thio}methyl)morpholine (37)

(2S)-2-((S)-(2-Fluorophenyl){[2-(methyloxy)phenyl]thio}methyl)-4-(phenylmethyl)morpholine (36a)

and (2R)-2-((R)-(2-Fluorophenyl){[2-(methyloxy)phenyl]thio}methyl)-4-(phenylmethyl)morpholine (36b)

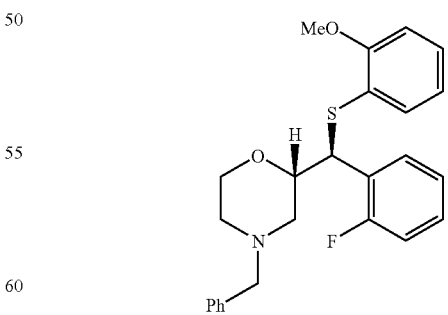

Compounds 36a,36b were obtained from 7a,7b (0.45 g, 1.17 mmol), cesium carbonate (0.42 g, 1.29 mmol, 1.1 eq), and 2-methoxy-thiophenol (0.82 g, 5.87 mmol) following a modification of General Procedure 1 in which the reaction mixture was heated to 95° C. for 2 hours and then stirred at room temperature for 18 hours. After purification by flash column chromatography (eluent: heptane/ethyl acetate 80/20 [v/v]) 36a,36 b was obtained as a colourless oil (0.36 g, 72%%); MW 423.55; $C_{25}H_{26}FNOS$; $^1$H NMR (CDCl$_3$): 6.65-7.5 (13H, m), 4.9 (1H, d, 7 Hz), 3.9-4.05 (2H, m), 3.8 (3H, s), 3.6 (1H, dt, 8 Hz and 1 Hz), 3.45 (1H, d, 13 Hz), 3.15 (1H, d, 13 Hz), 2.60 (2H, t, 8 Hz), 2.05-2.2 (2H, m); FIA: m/z 424 [M+H]$^+$.

(2S)-2-((S)-(2-Fluorophenyl){[2-(methyloxy)phenyl]thio}methyl)morpholine (37)

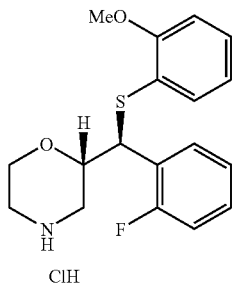

Compound 37 (Example 15) was obtained from 36a,36b (0.43 g, 1.02 mmol), solid supported Hünig's base (Argonaut, 3.56 mmol/g, 0.37 g, 1.12 mmol, 1.1 eq) and α-chloroethyl chloroformate (1.08 ml, 10.12 mmol, 10 eq) in anhydrous dichloromethane (5 ml) following General Procedure 2a as a colourless oil (0.34 g, 99%) after separation by chiral HPLC on a ChiralPak-AD semi-preparative column. Chiral LC: 12.86 min. LC purity=99.1 (UV$_{254\ nm}$); MW 369.89; $C_{18}H_{20}FNOS$; HA: m/z 334 [M+H]$^+$. 37 was converted into its hydrochloride salt following General Procedure 3; MW 333.43; $C_{18}H_{20}FNOS$; $^1$H NMR (CDCl$_3$): 7.2-7.3 (1H, m), 6.85-7.2 (8H, m), 4.85 (1H, d, 8 Hz), 3.95-4.15 (2H, m), 3.85.3.9 (3H, m), 3.7 (1H, dt, 1 Hz and 7 Hz), 2.6-3.0 (4H, m).

Example 16

2-[2-Methyl-1-(2-trifluoromethyl-phenylsulfanyl)-propyl]-morpholine (56)

4-Benzyl-2-(1-hydroxy-2-methyl-propyl)-morpholin-3-one (53)

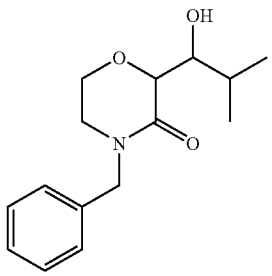

To a stirred solution of 2 (5.05 g, 26.4 mmol) in tetrahydrofuran (25 ml) at −78° C. under nitrogen was added lithium diisopropylamide (14.5 ml of a 2M solution, 29.0 mmol) dropwise over 40 minutes. The reaction mixture was stirred at the same temperature over 30 minutes after which time a solution of isobutyraldehyde (2.63 ml, 29.0 mmol) in tetrahydrofuran (15 ml) was added dropwise over 30 minutes. After one hour, the reaction mixture was allowed to warm to room temperature and quenched by addition of saturated ammonium chloride solution. Extraction with dichloromethane and drying over magnesium sulphate gave 53 as a mixture of diastereomers. Upon concentration in vacuo one diastereomer precipitated as a white solid (53a: 0.99 g). The remaining mother liquors were purified by column chromatography (30% ethyl acetate in hexane [v/v]) to give 53 (2.06 g). MW 263.34; $C_{15}H_{21}NO_3$; LCMS (6 min method): m/z 286 [M+Na]$^+$; RT=2.748.

1-(4-Benzyl-morpholin-2-yl)-2-methyl-propan-1-ol (54)

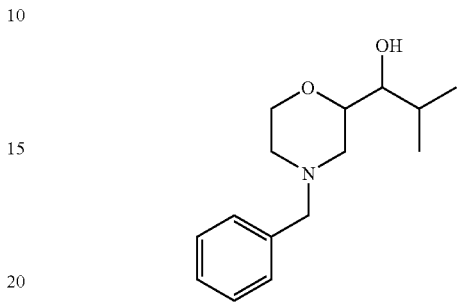

To a stirred solution of 53 (1.97 g, 7.47 mmol) in tetrahydrofuran (50 ml) at room temperature under nitrogen was added borane-tetrahydrofuran complex (30 ml of a 1M solution, ca 4 eq.). The reaction was heated to 60° C. and followed by TLC-analysis. When all starting material had been consumed a few drops of methanol were added followed by a similar amount of 1N hydrochloric acid and heating was continued for another hour. Organic solvents were removed in vacuo and the remaining solution was poured onto 1M potassium carbonate solution (30 ml), extracted with diethyl ether. The organic layers were dried over magnesium sulphate and purified by column chromatography (gradient from 15% ethyl acetate in hexane [v/v]) gave 54 (1.8 g, 97%). MW 249.36; $C_{15}H_{23}NO_2$; LCMS (6 min method): m/z 250 [M+H]$^+$; RT=0.838.

4-Benzyl-2-[2-methyl-1-(2-trifluoromethyl-phenylsulfanyl)-propyl]-morpholine (55)

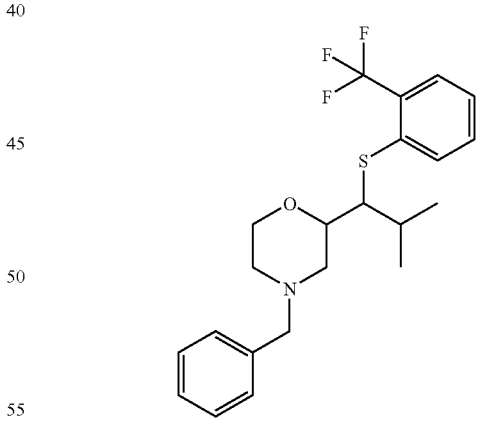

Compound 55 was obtained from 54 in a two-step procedure. To a stirred solution of 54 (1.8 g, 7.2 mmol) in dichloromethane (50 ml) at room temperature was added solid solid supported Hünig's base (Argonaut, 3.56 mmol/g, 6.2 g, 22 mmol, 3 eq) followed methanesulphonyl chloride (1.12 ml, 14 mmol). After stirring for one hour, the reaction mixture was filtered and the filtrates washed with brine and dried over magnesium sulphate to give the intermediate mesylate as a yellow oil (2.93 g of isolated crude product). The crude product was taken up in dry dimethylformamide (50 ml), 2-trifluoromethyl benzenethiol (2.1 ml, 14 mmol) and solid supported Hünig's base (Argonaut, 3.56 mmol/g, 0.55 g, 1.95 mmol) were added and the mixture heated to 70° C. and stirred for 72 hours. The reaction was quenched by addition of water (50 ml) and sodium hydroxide solution (70 ml of a 2N solution). The aqueous layer was extracted with diethyl ether (3×50 ml), washed with brine and dried over magnesium sulphate. Purification by ion-exchange chromatography followed by preparative HPLC gave 55. MW 409.52; $C_{22}H_{26}F_3NOS$; LCMS (6 min method): m/z 410 [M+H]$^+$; RT=3.398.

2-[2-Methyl-1-(2-trifluoromethyl-phenylsulfanyl)-propyl]-morpholine (56)

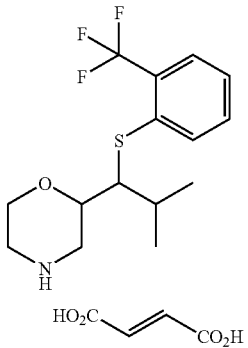

Compound 56 (Example 16) was obtained from 55 (0.8 g, 1.95 mmol), solid supported Hünig's base (Argonaut, 3.56 mmol/g, 1.65 g, 5.85 mmol, 3 eq) and α-chloroethyl chloroformate (0.4 ml, 3.9 mmol, 2 eq) in anhydrous dichloromethane (20 ml) following General Procedure 2a as a colourless oil (0.5 g, 85% yield). Chiral HPLC on a Chiral-Cel-OD(3671) column using 50% heptane in ethanol [v/v] gave 2 fractions (Rt=8.793 min and 10.443 min). Conversion into fumarate salt 56 was carried out by dissolving in diethyl ether and addition of small amount of methanol. Data for 56 derived from fraction with Rt=8.793 min: MW 435.46; $C_{19}H_{24}F_3NO_5S$; $^1$H NMR (d$_3$-MeOD): 6.2-6.3 (2H, m), 6.1-6.2 (1H, m), 5.2 (1H, s), 2.6-2.7 (2H, m), 2.2-2.4 (1H, m), 1.6-1.9 (4H, m), 1.6-1.7 (1H, m), –0.4-–0.5 (6H, m).

Example 17

2-[2-Methyl-1-(2-trifluoromethyl-phenoxy)-propyl]-morpholine (58)

4-Benzyl-2-[2-methyl-1-(2-trifluoromethyl-phenoxy)-propyl]-morpholine (57)

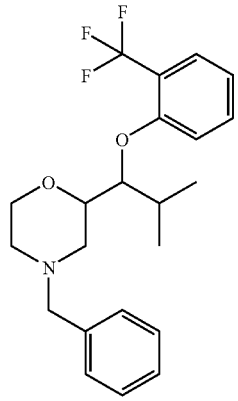

To a solution of 53a (0.146 g, 0.585 mmol) in dry dimethylformamide (2 ml) under nitrogen and ice-cooling was added sodium hydride (26 mg of a 60% dispersion in oil, 0.644 mmol) portionwise. The reaction was allowed to warm to room temperature for 30 minutes before addition of 2-fluoro-benzotriflouride (0.07 ml, 0.66 mmol). After stirring for 12 hours, another 0.5 equivalents of reagents were added and the reaction mixture heated to 40° C. for 30 minutes and then to 60° C. for another 2 hours. The crude reaction mixture was purified by ion-exchange column chromatography followed by preparative HPLC to give 57 (0.208 g, 92% yield) MW 393.45; $C_{22}H_{26}F_3NO_2$; LCMS (6 min method): m/z 394 [M+H]$^+$; RT=3.150.

2-[2-Methyl-1-(2-trifluoromethyl-phenoxy)-propyl]-morpholine (58)

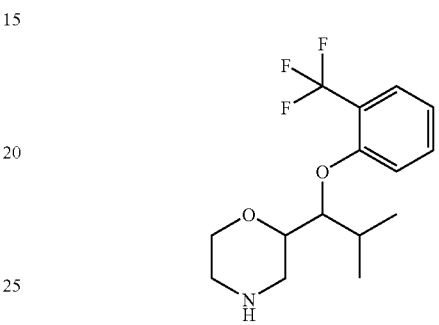

Compound 58 (Example 17) was obtained from 57 (0.21 g, 0.53 mmol), solid supported Hünig's base (Argonaut, 3.56 mmol/g, 0.45 g, 1.5 mmol, 3 eq) and α-chloroethyl chloroformate (0.11 ml, 1.06 mmol, 2 eq) in anhydrous dichloromethane (10 ml) following General Procedure 2 as a colourless oil (0.147 g, 92% yield) MW 303.33; $C_{15}H_{20}F_3NO_2$; $^1$H NMR (CDCl$_3$): 7.5-7.6 (1H, m), 7.2-7.4 (1H, m), 7.0-7.1 (1H, m), 6.8-6.95 (1H, m), 4.15-4.25 (1H, m), 3.6-3.9 (2H, m), 3.4-3.6 (1H, m), 2.6-2.9 (4H, m), 2.15 (1H, br, s)1.8-2.1 (1H, m), 1.1-1.2 (6H, m); LCMS (12 min method): m/z 304 [M+H]$^+$; RT=4.862.

The pharmacological profile of the present compounds may be demonstrated as follows. All of the exemplified compounds above have been found to exhibit a $K_i$ value less than 500 nM at the norepinephrine transporter as determined using the scintillation proximity assay described below. Furthermore, all of the exemplified compounds above have been found to selectively inhibit the norepinephrine transporter relative to the serotonin and dopamine transporters by a factor of at least five using the scintillation proximity assays as described below.

Generation of Stable Cell-lines Expressing the Human Dopamine, Norepinephrine and Serotonin Transporters Standard molecular cloning techniques were used to generate stable cell-lines expressing the human dopamine, norepinephrine and serotonin transporters. The polymerase chain reaction (PCR) was used in order to isolate and amplify each of the three full-length cDNAs from an appropriate cDNA library. Primers for PCR were designed using the following published sequence data:

Human dopamine transporter: GenBank M95167. Reference: Vandenbergh D J, Persico A M and Uhl G R. *A human dopamine transporter cDNA predicts reduced glycosylation, displays a novel repetitive element and provides racially-dimorphic TaqI RFLPs*. Molecular Brain Research (1992) volume 15, pages 161-166.

Human norepinephrine transporter: GenBank M65105. Reference: Pacholczyk T, Blakely, R D and Amara S G. *Expression cloning of a cocaine-and antidepressant-sensitive human noradrenaline transporter*. Nature (1991) volume 350, pages 350-354.

Human serotonin transporter: GenBank L05568. Reference: Ramamoorthy S, Bauman A L, Moore K R, Han H, Yang-Feng T, Chang A S, Ganaphthy V and Blakely R D. *Antidepressant-and cocaine-sensitive human serotonin transporter: Molecular cloning, expression, and chromosomal localization*. Proceedings of the National Academy of Sciences of the USA (1993) volume 90, pages 2542-2546.

The PCR products were cloned into a mammalian expression vector (eg pcDNA3.1 (Invitrogen)) using standard ligation techniques. The constructs were then used to stably transfect HEK293 cells using a commercially available lipofection reagent (Lipofectamine™—Invitrogen) following the manufacture's protocol.

Scintillation Proximity Assays for Determining the Affinity of Test Ligands at the Norepinephrine Transporter.

The compounds of the present invention are norepinephrine reuptake inhibitors, and possess excellent activity in, for example, a scintillation proximity assay (e.g. J. Gobel, D. L. Saussy and A. Goetz, J. Pharmacol. Toxicolo. (1999), 42, 237-244). Thus $^3$H-nisoxetine binding to norepinephrine re-uptake sites in a cell line transfected with DNA encoding human norepinephrine transporter binding protein has been used to determine the affinity of ligands at the norepinephrine transporter.

Membrane Preparation:

Cell pastes from large scale production of HEK-293 cells expressing cloned human norepinephrine transporters were homogenized in 4 volumes 50 mM Tris-HCl containing 300 mM NaCl and 5 mM KCl, pH 7.4. The homogenate was centrifuged twice (40,000 g, 10 min, 4° C.) with pellet re-suspension in 4 volumes of Tris-HCl buffer containing the above reagents after the first spin and 8 volumes after the second spin. The suspended homogenate was centrifuged (100 g, 10 min, 4° C.) and the supernatant kept and re-centrifuged (40,000 g, 20 min, 4° C.). The pellet was resuspended in Tris-HCl buffer containing the above reagents along with 10% w/v sucrose and 0.1 mM phenylmethylsulfonyl fluoride (PMSF). The membrane preparation was stored in aliquots (1 ml) at −80° C. until required. The protein concentration of the membrane preparation was determined using a bicinchoninic acid (BCA) protein assay reagent kit (available from Pierce).

[$^3$]-Nisoxetine Binding Assay:

Each well of a 96 well microtitre plate was set up to contain the following:

50 µl 2 nM [N-methyl-$^3$H]-Nisoxetine hydrochloride (70-87 Ci/mmol, from NEN life Science Products)

75 µl Assay buffer (50 mM Tris-HCl pH 7.4 containing 300 mM NaCl and 5 mM KCl)

25 µl Test compound, assay buffer (total binding) or 10 µM Desipramine HCl (non-specific binding)

50 µl Wheatgerm agglutinin coated poly (vinyltoluene) (WGA PVT) SPA Beads (Amersham Biosciences RPNQ0001) (10 mg/ml)

50 µl Membrane (0.2 mg protein per ml)

The microtitre plates were incubated at room temperature for 10 hours prior to reading in a Trilux scintillation counter. The results were analysed using an automatic spline fitting programme (Multicalc, Packard, Milton Keynes, UK) to provide Ki values for each of the test compounds.

Serotonin Binding Assay

The ability of a test compound to compete with [$^3$H]-citalopram for its binding sites on cloned human serotonin transporter containing membranes has been used as a measure of test compound ability to block serotonin uptake via its specific transporter (Ramamoorthy, S., Giovanetti, E., Qian, Y., Blakely, R., (1998) J. Biol. Chem. 273, 2458).

Membrane Preparation:

Membrane preparation is essentially similar to that for the norepinephrine transporter containing membranes as described above. The membrane preparation was stored in aliquots (1 ml) at −70° C. until required. The protein concentration of the membrane preparation was determined using a BCA protein assay reagent kit.

[$^3$H]-Citalopram Binding Assay:

Each well of a 96 well microtitre plate was set up to contain the following:

50 µl 2 nM [$^3$H]-Citalopram (60-86 Ci/mmol, Amersham Biosciences)

75 µl Assay buffer (50 mM Tris-HCl pH 7.4 containing 150 mM NaCl and 5 mM KCl)

25 µl Diluted compound, assay buffer (total binding) or 100 µM Fluoxetine (non-specific binding)

50 µl WGA PVT SPA Beads (40 mg/ml)

50 µl Membrane preparation (0.4 mg protein per ml)

The microtitre plates were incubated at room temperature for 10 hours prior to reading in a Trilux scintillation counter. The results were analysed using an automatic spline fitting programme (Multicalc, Packard, Milton Keynes, UK) to provide Ki (nM) values for each of the unknown compounds.

Dopamine Binding Assay

The ability of a test compound to compete with [$^3$H]-WIN35,428 for its binding sites on human cell membranes containing cloned human dopamine transporter has been used as a measure of the ability of such test compounds to block dopamine uptake via its specific transporter (Ramamoorthy et al 1998 supra).

Membrane Preparation:

Is essentially the same as for membranes containing cloned human serotonin transporter as described above.

[$^3$H]-WIN35,428 Binding Assay:

Each well of a 96well microtitre plate was set up to contain the following:

50 µl 4 nM [$^3$H]-WIN35,428 (84-87 Ci/mmol, from NEN Life Science Products)

75 µl Assay buffer (50 mM Tris-HCl pH 7.4 containing 150 mM NaCl and 5 mM KCl)

25 µl Diluted compound, assay buffer (total binding) or 100 µM Nomifensine (non-specific binding)

50 µl WGA PVT SPA Beads (10 mg/ml)

50 µl Membrane preparation (0.2 mg protein per ml.)

The microtitre plates were incubated at room temperature for 120 minutes prior to reading in a Trilux scintillation counter. The results were analysed using an automatic spline fitting programme (Multicalc, Packard, Milton Keynes, UK) to provide Ki values for each of the unknown compounds.

In Vitro Determination of the Interaction of Compounds with CYP2D6 in Human Hepatic Microsomes Cytochrome P450 2D6 (CYP2D6) is a mammalian enzyme which is commonly associated with the metabolism of around 30% of pharmaceutical compounds. Moreover, this enzyme shows a genetic polymorphism with as a consequence a presence in the population of poor and normal metabolizers. A low involvement of CYP2D6 in the metabolism of compounds (i.e. the compound being a poor substrate of CYP2D6) is desirable in order to reduce any variability from subject to subject in the pharmacokinetics of the compound. Also, compounds with a low inhibitor potential for CYP2D6 are desirable in order to avoid drug-drug interactions with co-administered drugs that are substrates of CYP2D6. Compounds may be tested both as substrates and as inhibitors of this enzyme by means of the following assays.

CYP2D6 Substrate Assay

Principle:

This assay determines the extent of the CYP2D6 enzyme involvement in the total oxidative metabolism of a compound in microsomes. Preferred compounds of the present invention exhibit less than 75% total metabolism via the CYP2D6 pathway.

For this in vitro assay, the extent of oxidative metabolism in human liver microsomes (HLM) is determined after a 30 minute incubation in the absence and presence of Quinidine, a specific chemical inhibitor of CYP2D6. The difference in the extent of metabolism in absence and presence of the inhibitor indicates the involvement of CYP2D6 in the metabolism of the compound.

Materials and Methods:

Human liver microsomes (mixture of 20 different donors, mixed gender) were acquired from Human Biologics (Scottsdale, Ariz., USA). Quinidine and β-NADPH (β-Nicotinamide Adenine Dinucleotide Phosphate, reduced form, tetrasodium salt) were purchased from Sigma (St Louis, Mo., USA). All the other reagents and solvents were of analytical grade. A stock solution of the new chemical entity (NCE) was prepared in a mixture of Acetonitrile/Water to reach a final concentration of acetonitrile in the incubation below 0.5%.

The microsomal incubation mixture (total volume 0.1 mL) contained the NCE (4 µM), β-NADPH (1 mM), microsomal proteins (0.5 mg/mL), and Quinidine (0 or 2 µM) in 100 mM sodium phosphate buffer pH 7.4. The mixture was incubated for 30 minutes at 37° C. in a shaking waterbath. The reaction was terminated by the addition of acetonitrile (75 µL). The samples were vortexed and the denaturated proteins were removed by centrifugation. The amount of NCE in the supernatant was analyzed by liquid chromatography/mass spectrometry (LC/MS) after addition of an internal standard. A sample was also taken at the start of the incubation (t=0), and analysed similarly.

Analysis of the NCE was performed by liquid chromatography/mass spectrometry. Ten µL of diluted samples (20 fold dilution in the mobile phase) were injected onto a Spherisorb CN Column, 5 µM and 2.1 mm×100 mm (Waters corp. Milford, Mass., USA). The mobile phase consisting of a mixture of Solvent A/Solvent B, 30/70 (v/v) was pumped (Alliance 2795, Waters corp. Milford, Mass., USA) through the column at a flow rate of 0.2 ml/minute. Solvent A and Solvent B were a mixture of ammonium formate $5.10^{-3}$ M pH 4.5/methanol in the proportions 95/5 (v/v) and 10/90 (v/v), for solvent A and solvent B, respectively. The NCE and the internal standard were quantified by monitoring their molecular ion using a mass spectrometer ZMD or ZQ (Waters-Micromass corp, Machester, UK) operated in a positive electrospray ionisation.

The extent of CYP2D6 involvement (% of CYP2D6 involvement) was calculated comparing the extent of metabolism in absence and in presence of quinidine in the incubation.

The extent of metabolism without inhibitor (%) was calculated as follows:

$$\frac{(NCE \text{ response in samples without inhibitor)time } 0 - (NCE \text{ response in samples without inhibitor)time } 30}{(NCE \text{ response in samples without inhibitor)time } 0} \times 100$$

The extent of metabolism with inhibitor (%) was calculated as follows:

$$\frac{(NCE \text{ response in samples without inhibitor)time } 0 - (NCE \text{ response in samples with inhibitor)time } 30}{(NCE \text{ response in samples without inhibitor)time } 0} \times 100$$

where the NCE response is the area of the NCE divided by the area of the internal standard in the LC/MS analysis chromatogram, time0 and time30 correspond to the 0 and 30 minutes incubation time.

The % of CYP2D6 involvement was calculated as follows:

$$\frac{(\% \text{ extent of metabolism without inhibitor}) - (\% \text{ extent of metabolism with inhibitor})}{\% \text{ extent of metabolism without inhibitor}} \times 100$$

CYP2D6 Inhibitor Assay

Principle:

The CYP2D6 inhibitor assay evaluates the potential for a compound to inhibit CYP2D6. This is performed by the measurement of the inhibition of the bufuralol 1'-hydroxylase activity by the compound compared to a control. The 1'-hydroxylation of bufuralol is a metabolic reaction specific to CYP2D6. Preferred compounds of the present invention exhibit an $IC_{50}$ higher than 6 µM for CYP2D6 activity, the $IC_{50}$ being the concentration of the compound that gives 50% of inhibition of the CYP2D6 activity.

Material and Methods:

Human liver microsomes (mixture of 20 different donors, mixed gender) were acquired from Human Biologics (Scottsdale, Ariz.). β-NADPH was purchased from Sigma (St Louis, Mo.). Bufuralol was purchased from Ultrafine (Manchester, UK). All the other reagents and solvents were of analytical grade.

Microsomal incubation mixture (total volume 0.1 mL) contained bufuralol 10 µM, β-NADPH (2 mM), microsomal proteins (0.5 mg/mL), and the new chemical entity (NCE) (0, 5, and 25 µM) in 100 mM sodium phosphate buffer pH 7.4. The mixture was incubated in a shaking waterbath at 37° C. for 5 minutes. The reaction was terminated by the addition of methanol (75 µL). The samples were vortexed and the denaturated proteins were removed by centrifugation. The supernatant was analyzed by liquid chromatography connected to a fluorescence detector. The formation of the 1'-hydroxybufuralol was monitored in control samples (0 µM NCE) and in the samples incubated in presence of the NCE. The stock solution of NCE was prepared in a mixture of Acetonitrile/Water to reach a final concentration of acetonitrile in the incubation below 1.0%.

The determination of 1'-hydroxybufuralol in the samples was performed by liquid chromatograhy with fluorimetric detection as described below. Twenty five µL samples were injected onto a Chromolith Performance RP-18e column (100 mm×4.6 mm) (Merck KGAa, Darmstadt, Germany). The mobile phase, consisting of a mixture of solvent A and solvent B whose the proportions changed according the following linear gradient, was pumped through the column at a flow rate of 1 ml/min:

| Time (minutes) | Solvent A (%) | Solvent B (%) |
|---|---|---|
| 0 | 65 | 35 |
| 2.0 | 65 | 35 |
| 2.5 | 0 | 100 |
| 5.5 | 0 | 100 |
| 6.0 | 65 | 35 |

Solvent A and Solvent B consisted of a mixture of 0.02 M potassium dihydrogenophosphate buffer pH3/methanol in the proportion 90/10 (v/v) for solvent A and 10/90 (v/v) for solvent B. The run time was 7.5 minutes. Formation of 1'-hydroxybufuralol was monitored by fluorimetric detection with extinction at λ 252 nm and emission at λ 302 nm.

The $IC_{50}$ of the NCE for CYP2D6 was calculated by the measurement of the percent of inhibition of the formation of the 1'-hydroxybufuralol in presence of the NCE compared to control samples (no NCE) at a known concentration of the NCE.

The percent of inhibition of the formation of the 1'-hydroxybufuralol is calculated as follows:

$$\frac{(1'\text{-hydroxybufuralol formed without inhibitor}) - (1'\text{-hydroxybufuralol formed with inhibitor})}{(1'\text{-hydroxybufuralol area formed without inhibitor})} \times 100$$

The $IC_{50}$ is calculated from the percent inhibition of the formation of the 1'-hydroxybufuralol as follows (assuming competitive inhibition):

$$\frac{NCE \text{ Concentration} \times (100 - \text{Percent of inhibition})}{\text{Percent of inhibition}}$$

The $IC_{50}$ estimation is assumed valid if inhibition is between 20% and 80% (Moody G C, Griffin S J, Mather A N, McGinnity D P, Riley R J. 1999. Fully automated analysis of activities catalyzed by the major human liver cytochrome P450 (CYP) enzymes: assessment of human CYP inhibition potential. Xenobiotica, 29(1): 53-75).

X-Ray Crystallographic Data for the Compound of Example 1

TABLE 1

Crystal data and structure refinement for 2003xf.

| | |
|---|---|
| Identification code | 2003xf |
| Empirical formula | C18H19ClF3NOS |
| Formula weight | 389.85 |
| Temperature | 107(2) K |
| Wavelength | 0.71073 A |
| Crystal system, space group | Monoclinic, P2(1) |
| Unit cell dimensions | a = 9.984(2) A   alpha = 90 deg. |
| | b = 5.6484(13) A   beta = 100.867(4) deg. |
| | c = 15.931(4) A   gamma = 90 deg. |
| Volume | 882.4(4) A^3 |
| Z, Calculated density | 2, 1.467 Mg/m^3 |
| Absorption coefficient | 0.371 mm^-1 |
| F(000) | 404 |
| Crystal size | .06 × .08 × .18 mm |
| Theta range for data collection | 1.30 to 28.20 deg. |
| Limiting indices | 11 <= h <= 13, -7 <= k <= 7, -20 <= l <= 19 |
| Reflections collected/unique | 5986/3378 [R(int) = 0.0661] |
| Completeness to theta = 28.20 | 92.9% |
| Absorption correction | None |
| Refinement method | Full-matrix least-squares on F^2 |
| Data/restraints/parameters | 3378/1/234 |
| Goodness-of-fit on F^2 | 0.846 |
| Final R indices [I > 2 sigma(I)] | R1 = 0.0488, wR2 = 0.0908 |
| R indices (all data) | R1 = 0.1227, wR2 = 0.1101 |
| Absolute structure parameter | 0.11(10) |
| Largest diff. peak and hole | 0.548 and -0.444 e.A^-3 |

X-Ray Crystallographic Data for the Compound of Example 1

TABLE 2

Atomic coordinates (×10^4) and equivalent isotropic displacement parameters (A^2 × 10^3) for 2003xf.
U(eq) is defined as one third of the trace of the orthogonalized Uij tensor.

| | x | y | z | U(eq) |
|---|---|---|---|---|
| S(8) | 8641(1) | 5291(2) | 2641(1) | 35(1) |
| O(1) | 10279(3) | 2645(5) | 4200(2) | 24(1) |
| C(7) | 9992(5) | 3088(8) | 2678(3) | 25(1) |
| F(3) | 5136(4) | 4842(7) | 443(2) | 65(1) |
| N(4) | 13055(4) | 1352(9) | 4386(3) | 21(1) |
| C(5) | 12147(4) | 1431(8) | 3536(3) | 22(1) |
| F(2) | 7264(4) | 4253(5) | 644(2) | 51(1) |
| C(20) | 10490(5) | 1794(8) | 1263(3) | 31(1) |
| F(1) | 6497(4) | 7227(5) | 1228(2) | 48(1) |
| C(15) | 10669(5) | 3416(8) | 1925(3) | 24(1) |
| C(6) | 11008(5) | 3187(8) | 3525(3) | 24(1) |
| C(16) | 11472(5) | 5394(10) | 1846(3) | 32(1) |
| C(10) | 6184(5) | 3389(9) | 1805(3) | 26(1) |
| C(13) | 5978(5) | 382(11) | 3117(4) | 40(1) |
| C(9) | 7190(5) | 3438(9) | 2506(3) | 30(1) |
| C(3) | 12283(5) | 976(8) | 5085(3) | 27(1) |
| C(12) | 4992(5) | 364(10) | 2423(3) | 31(1) |
| C(2) | 11168(5) | 2787(9) | 5010(3) | 28(1) |
| C(21) | 6253(6) | 4934(11) | 1033(4) | 41(2) |
| C(18) | 11846(5) | 4080(10) | 494(3) | 33(1) |
| C(17) | 12048(5) | 5721(9) | 1131(4) | 36(1) |
| C(19) | 11078(5) | 2138(9) | 552(4) | 35(1) |
| C(11) | 5062(5) | 1943(9) | 1738(4) | 42(2) |
| C(14) | 7065(6) | 1852(10) | 3160(4) | 43(2) |
| Cl(1) | 4131(1) | 6360(2) | 4214(1) | 30(1) |

X-Ray Crystallographic Data for the Compound of Example 1

TABLE 3

Bond lengths [A] and angles [deg] for 2003xf.

| | |
|---|---|
| S(8)—C(9) | 1.767(5) |
| S(8)—C(7) | 1.828(5) |
| O(1)—C(2) | 1.424(5) |
| O(1)—C(6) | 1.440(5) |
| C(7)—C(15) | 1.495(6) |
| C(7)—C(6) | 1.528(6) |
| F(3)—C(21) | 1.318(6) |
| N(4)—C(5) | 1.481(5) |
| N(4)—C(3) | 1.484(6) |
| C(5)—C(6) | 1.507(6) |
| F(2)—C(21) | 1.337(6) |
| C(20)—C(19) | 1.385(7) |
| C(20)—C(15) | 1.383(6) |
| F(1)—C(21) | 1.343(6) |
| C(15)—C(16) | 1.395(6) |
| C(16)—C(17) | 1.382(7) |
| C(10)—C(9) | 1.354(6) |
| C(10)—C(11) | 1.374(7) |
| C(10)—C(21) | 1.520(8) |
| C(13)—C(12) | 1.334(6) |

TABLE 3-continued

Bond lengths [A] and angles [deg] for 2003xf.

| | |
|---|---|
| C(13)—C(14) | 1.358(7) |
| C(9)—C(14) | 1.397(7) |
| C(3)—C(2) | 1.500(6) |
| C(12)—C(11) | 1.421(7) |
| C(18)—C(19) | 1.351(7) |
| C(18)—C(17) | 1.360(7) |
| C(9)—S(8)—C(7) | 100.6(2) |
| C(2)—O(1)—C(6) | 110.4(4) |
| C(15)—C(7)—C(6) | 112.3(4) |
| C(15)—C(7)—S(8) | 109.4(3) |
| C(6)—C(7)—S(8) | 111.5(3) |
| C(5)—N(4)—C(3) | 112.0(4) |
| N(4)—C(5)—C(6) | 11.2(4) |
| C(19)—C(20)—C(15) | 121.2(5) |
| C(20)—C(15)—C(16) | 117.1(5) |
| C(20)—C(15)—C(7) | 121.1(5) |
| C(16)—C(15)—C(7) | 121.8(5) |
| O(1)—C(6)—C(5) | 109.7(4) |
| O(1)—C(6)—C(7) | 107.9(4) |
| C(5)—C(6)—C(7) | 111.1(4) |
| C(17)—C(16)—C(15) | 121.2(5) |
| C(9)—C(10)—C(11) | 122.9(5) |
| C(9)—C(10)—C(21) | 121.0(5) |
| C(11)—C(10)—C(21) | 116.0(5) |
| C(12)—C(13)—C(14) | 120.3(6) |
| C(10)—C(9)—C(14) | 116.4(5) |
| C(10)—C(9)—S(8) | 125.2(4) |
| C(14)—C(9)—S(8) | 118.4(4) |
| N(4)—C(3)—C(2) | 109.0(4) |
| C(13)—C(12)—C(11) | 119.7(5) |
| O(1)—C(2)—C(3) | 111.1(4) |
| F(3)—C(21)—F(1) | 107.1(5) |
| F(3)—C(21)—F(2) | 105.6(5) |
| F(1)—C(21)—F(2) | 105.4(5) |
| F(3)—C(21)—C(10) | 113.2(5) |
| F(1)—C(21)—C(10) | 113.6(5) |
| F(2)—C(21)—C(10) | 111.4(5) |
| C(19)—C(18)—C(17) | 120.6(5) |
| C(18)—C(17)—C(16) | 119.8(5) |
| C(18)—C(19)—C(20) | 120.2(5) |
| C(10)—C(11)—C(12) | 118.1(5) |
| C(13)—C(14)—C(9) | 122.5(5) |

Symmetry transformations used to generate equivalent atoms:

X-Ray Crystallographic Data for the Compound of Example 1

TABLE 4

Anisotropic displacement parameters (A^2 × 10^3) for 2003xf. The anisotropic displacement factor exponent takes the form: $-2\pi^2 [h^2 a^{*2} U11 + \ldots + 2 h k a^* b^* U12]$

| | U11 | U22 | U33 | U23 | U13 | U12 |
|---|---|---|---|---|---|---|
| S(8) | 24(1) | 24(1) | 53(1) | −1(1) | −1(1) | 4(1) |
| O(1) | 24(2) | 23(2) | 24(2) | 0(2) | 0(2) | −2(2) |
| C(7) | 20(3) | 23(2) | 27(3) | −3(2) | −8(3) | 0(2) |
| F(3) | 55(2) | 88(3) | 42(2) | 15(2) | −16(2) | −13(2) |
| N(4) | 19(2) | 14(2) | 31(3) | 3(2) | 3(2) | −3(3) |
| C(5) | 22(3) | 16(2) | 26(3) | −4(2) | 2(2) | 2(3) |
| F(2) | 69(2) | 53(2) | 39(2) | 5(2) | 29(2) | 3(2) |
| C(20) | 29(3) | 28(3) | 31(3) | −12(3) | −5(3) | −1(2) |
| F(1) | 61(2) | 35(2) | 46(2) | 5(2) | 5(2) | 5(2) |
| C(15) | 20(3) | 22(3) | 27(3) | 2(3) | −3(2) | 5(2) |
| C(6) | 23(3) | 17(2) | 33(3) | −1(2) | 11(3) | 1(2) |
| C(16) | 40(3) | 22(2) | 31(3) | −3(3) | 1(3) | −7(3) |
| C(10) | 20(3) | 30(3) | 27(3) | 2(3) | 8(3) | 4(3) |
| C(13) | 33(3) | 45(3) | 42(4) | 3(3) | 7(3) | 0(3) |
| C(9) | 20(3) | 38(3) | 31(4) | −8(3) | 2(3) | 7(3) |

TABLE 4-continued

Anisotropic displacement parameters (A^2 × 10^3) for 2003xf. The anisotropic displacement factor exponent takes the form: $-2\pi^2 [h^2 a^{*2} U11 + \ldots + 2 h k a^* b^* U12]$

| | U11 | U22 | U33 | U23 | U13 | U12 |
|---|---|---|---|---|---|---|
| C(3) | 22(3) | 28(3) | 32(3) | 10(2) | 5(2) | 0(2) |
| C(12) | 22(3) | 29(2) | 41(4) | −1(3) | 8(3) | −7(3) |
| C(2) | 28(3) | 34(3) | 22(3) | −2(3) | 3(3) | 4(2) |
| C(21) | 27(4) | 50(4) | 43(4) | −16(3) | −1(3) | 10(3) |
| C(18) | 24(3) | 44(3) | 30(4) | −1(3) | 3(3) | 11(3) |
| C(17) | 42(4) | 26(3) | 40(4) | 0(3) | 9(3) | −6(2) |
| C(19) | 33(3) | 38(3) | 33(4) | −9(3) | 2(3) | 6(3) |
| C(11) | 20(3) | 49(4) | 52(4) | −18(3) | −3(3) | 8(3) |
| C(14) | 35(4) | 72(5) | 22(3) | 16(3) | −1(3) | −4(3) |
| Cl(1) | 24(1) | 16(1) | 46(1) | 1(1) | −1(1) | −1(1) |

X-Ray Crystallographic Data for the Compound of Example 1

TABLE 5

Hydrogen coordinates (×10^4) and isotropic displacement parameters (A^2 × 10^3) for 2003xf.

| | x | y | z | U(eq) |
|---|---|---|---|---|
| H(7A) | 9558 | 1486 | 2630 | 30 |
| H(5A) | 11757 | −162 | 3392 | 26 |
| H(5B) | 12685 | 1877 | 3099 | 26 |
| H(20A) | 9954 | 420 | 1297 | 37 |
| H(6A) | 11398 | 4819 | 3611 | 29 |
| H(16A) | 11626 | 6536 | 2292 | 38 |
| H(13A) | 5919 | −637 | 3583 | 48 |
| H(3A) | 12902 | 1128 | 5645 | 33 |
| H(3B) | 11886 | −636 | 5043 | 33 |
| H(12A) | 4246 | −700 | 2387 | 37 |
| H(2A) | 10639 | 2529 | 5468 | 34 |
| H(2B) | 11575 | 4389 | 5085 | 34 |
| H(18A) | 12248 | 4302 | 5 | 40 |
| H(17A) | 12584 | 7087 | 1084 | 43 |
| H(19A) | 10941 | 1005 | 103 | 42 |
| H(11A) | 4354 | 1998 | 1248 | 50 |
| H(14A) | 7767 | 1799 | 3653 | 52 |
| H(4B) | 13680(60) | 2600(100) | 4430(30) | 53(19) |
| H(4A) | 13580(50) | 230(90) | 4400(30) | 29(17) |

X-Ray Crystallographic Data for the Compound of Example 1

TABLE 6

Torsion angles [deg] for 2003xf.

| | |
|---|---|
| C(9)—S(8)—C(7)—C(15) | 115.5(4) |
| C(9)—S(8)—C(7)—C(6) | −119.7(4) |
| C(3)—N(4)—C(5)—C(6) | 52.2(6) |
| C(19)—C(20)—C(15)—C(16) | −0.4(7) |
| C(19)—C(20)—C(15)—C(7) | 177.8(4) |
| C(6)—C(7)—C(15)—C(20) | 126.4(5) |
| S(8)—C(7)—C(15)—C(20) | −109.2(4) |
| C(6)—C(7)—C(15)—C(16) | −55.5(6) |
| S(8)—C(7)—C(15)—C(16) | 68.9(5) |
| C(2)—O(1)—C(6)—C(5) | 60.7(5) |
| C(2)—O(1)—C(6)—C(7) | −178.1(4) |
| N(4)—C(5)—C(6)—O(1) | −55.1(5) |
| N(4)—C(5)—C(6)—C(7) | −174.3(4) |
| C(15)—C(7)—C(6)—O(1) | −175.0(4) |
| S(8)—C(7)—C(6)—O(1) | 61.9(4) |
| C(15)—C(7)—C(6)—C(5) | −54.7(5) |

TABLE 6-continued

Torsion angles [deg] for 2003xf.

| | |
|---|---|
| S(8)—C(7)—C(6)—C(5) | -177.8(3) |
| C(20)—C(15)—C(16)—C(17) | 0.7(7) |
| C(7)—C(15)—C(16)—C(17) | -177.4(5) |
| C(11)—C(10)—C(9)—C(14) | 2.6(8) |
| C(21)—C(10)—C(9)—C(14) | -176.4(5) |
| C(11)—C(10)—C(9)—S(8) | -178.8(4) |
| C(21)—C(10)—C(9)—S(8) | 2.2(7) |
| C(7)—S(8)—C(9)—C(10) | -114.6(5) |
| C(7)—S(8)—C(9)—C(14) | 64.0(5) |
| C(5)—N(4)—C(3)—C(2) | -52.6(6) |
| C(14)—C(13)—C(12)—C(11) | -1.9(8) |
| C(6)—O(1)—C(2)—C(3) | -63.3(5) |
| N(4)—C(3)—C(2)—O(1) | 58.2(5) |
| C(9)—C(10)—C(21)—F(3) | -173.8(5) |
| C(11)—C(10)—C(21)—F(3) | 7.1(7) |
| C(9)—C(10)—C(21)—F(1) | -51.3(7) |
| C(11)—C(10)—C(21)—F(1) | 129.6(5) |
| C(9)—C(10)—C(21)—F(2) | 67.4(7) |
| C(11)—C(10)—C(21)—F(2) | -111.6(5) |
| C(19)—C(18)—C(17)—C(16) | 0.5(8) |
| C(15)—C(16)—C(17)—C(18) | -0.7(8) |
| C(17)—C(18)—C(19)—C(20) | -0.2(8) |
| C(15)—C(20)—C(19)—C(18) | 0.1(8) |
| C(9)—C(10)—C(11)—C(12) | -2.7(8) |
| C(21)—C(10)—C(11)—C(12) | 176.3(5) |
| C(13)—C(12)—C(11)—C(10) | 2.3(8) |
| C(12)—C(13)—C(14)—C(9) | 1.9(8) |
| C(10)—C(9)—C(14)—C(13) | -2.1(8) |
| S(8)—C(9)—C(14)—C(13) | 179.2(4) |

Symmetry transformations used to generate equivalent atoms

The invention claimed is:

1. A compound of formula (II):

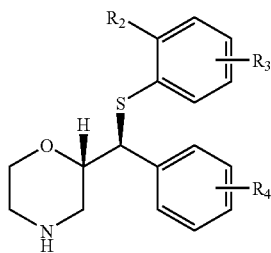

wherein:

$R_2$ and $R_3$ are each independently selected from H, $C_1$-$C_4$ alkyl, O($C_1$-$C_4$ alkyl), S($C_1$-$C_4$ alkyl), halo, and phenyl; and $R_4$ is selected from H and $C_1$-$C_4$ alkyl;

wherein each above-mentioned $C_1$-$C_4$ alkyl group is optionally substituted with one or more halo atoms;

and pharmaceutically acceptable salts thereof.

2. The compound of claim 1, wherein $R_2$ is selected from $C_1$-$C_4$ alkyl, O($C_1$-$C_4$ alkyl), F, and Ph, wherein each above-mentioned $C_1$-$C_4$ alkyl group is optionally substituted with one or more halo atoms.

3. The compound of claim 1, wherein $R_3$ is hydrogen.

4. The compound of claim 1, wherein $R_4$ is hydrogen.

5. A composition, comprising a compound of claim 1, or a pharmaceutically acceptable salt thereof, together with a pharmaceutically acceptable diluent, excipient, or carrier.

6. The compound of claim 1, where $R_2$ is trifluoromethyl, methoxy, trifluoromethoxy, F, or phenyl.

7. The compound of claim 1, where $R_3$ if F.

8. A method of preparing a compound of claim 1, comprising deprotecting a compound of the following formula:

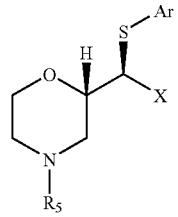

wherein:

R5 is a protecting group;

X is a phenyl group optionally substituted with 1 substituent which is C1-4 alkyl; and Ar is a phenyl group optionally substituted with 1 or 2 substituents each independently selected from C1-4 alkyl, O(C1-4alkyl), S(C1-4alkyl), halo and phenyl;

wherein each above-mentioned C1-4alkyl group is optionally substituted with one or more halo atoms; to provide a compound of claim 1, optionally followed by the step of forming a pharmaceutically acceptable salt.

* * * * *